(12) United States Patent
Martin

(10) Patent No.: US 8,177,957 B2
(45) Date of Patent: May 15, 2012

(54) MULTIPLE FREQUENCY METHOD FOR OPERATING ELECTROCHEMICAL SENSORS

(75) Inventor: Louis P. Martin, San Ramon, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 1034 days.

(21) Appl. No.: 11/893,751

(22) Filed: Aug. 16, 2007

(65) Prior Publication Data

US 2008/0067080 A1 Mar. 20, 2008

Related U.S. Application Data

(60) Provisional application No. 60/839,500, filed on Aug. 22, 2006.

(51) Int. Cl.
*G01N 27/407* (2006.01)
(52) U.S. Cl. ............ 205/781; 204/424; 204/425
(58) Field of Classification Search .......... 204/400, 204/424, 425, 431, 432; 205/775, 781, 783, 205/784
See application file for complete search history.

(56) References Cited

U.S. PATENT DOCUMENTS

| | | | |
|---|---|---|---|
| 4,376,026 A | 3/1983 | Hoffman et al. | |
| 4,407,704 A * | 10/1983 | Mase et al. | 205/785 |
| 4,419,190 A * | 12/1983 | Dietz et al. | 205/785 |
| 4,935,107 A * | 6/1990 | Picard et al. | 205/782 |
| 5,425,867 A | 6/1995 | Dawson et al. | |
| 6,096,186 A | 8/2000 | Warburton | |
| 6,143,165 A | 11/2000 | Kurosawa et al. | |
| 6,551,497 B1 | 4/2003 | Gao et al. | |
| 6,645,368 B1 * | 11/2003 | Beaty et al. | 205/792 |
| 7,597,793 B2 * | 10/2009 | Burke et al. | 205/792 |
| 2005/0069892 A1 | 3/2005 | Iyengar et al. | |
| 2006/0049048 A1 | 3/2006 | Kondo et al. | |

OTHER PUBLICATIONS

Wu et al, Sensors and Actuators B 110, 2005, pp. 49-53.*
Nakatou, M., et al., "Detection of combustible hydrogen-containing gases by using impedancemetric zirconia-based water-vapor sensor," Solid State Ionics, 176 (2005) 2511-2515.
Miura, N., et al., "Impedancemetric gas sensor based on zirconia solid electrolyte and oxide sensing elecrode for detecting total NOx at high temperature," Sensors and Acuators B 93 (2003) 221-228.
Martin, L. Peter, et al., "Impedancemetric NOx Sensing Usines YSZ Electrolyte and YSZ/CR2O3 Composite Electrodes," Journal of the Electrochemical Society, 154 (3) J97-J104 (2007).
Nakatou, M., et al., "Impedancemetric sensor based on YSZ and IN2O3 for detection of low concentrations of water vapor at high temperature," Electrochemistry Communications 6 (2004) 995-998.

* cited by examiner

*Primary Examiner* — Kaj K Olsen
(74) *Attorney, Agent, or Firm* — Eddie E. Scott

(57) ABSTRACT

A multiple frequency method for the operation of a sensor to measure a parameter of interest using calibration information including the steps of exciting the sensor at a first frequency providing a first sensor response, exciting the sensor at a second frequency providing a second sensor response, using the second sensor response at the second frequency and the calibration information to produce a calculated concentration of the interfering parameters, using the first sensor response at the first frequency, the calculated concentration of the interfering parameters, and the calibration information to measure the parameter of interest.

6 Claims, 20 Drawing Sheets

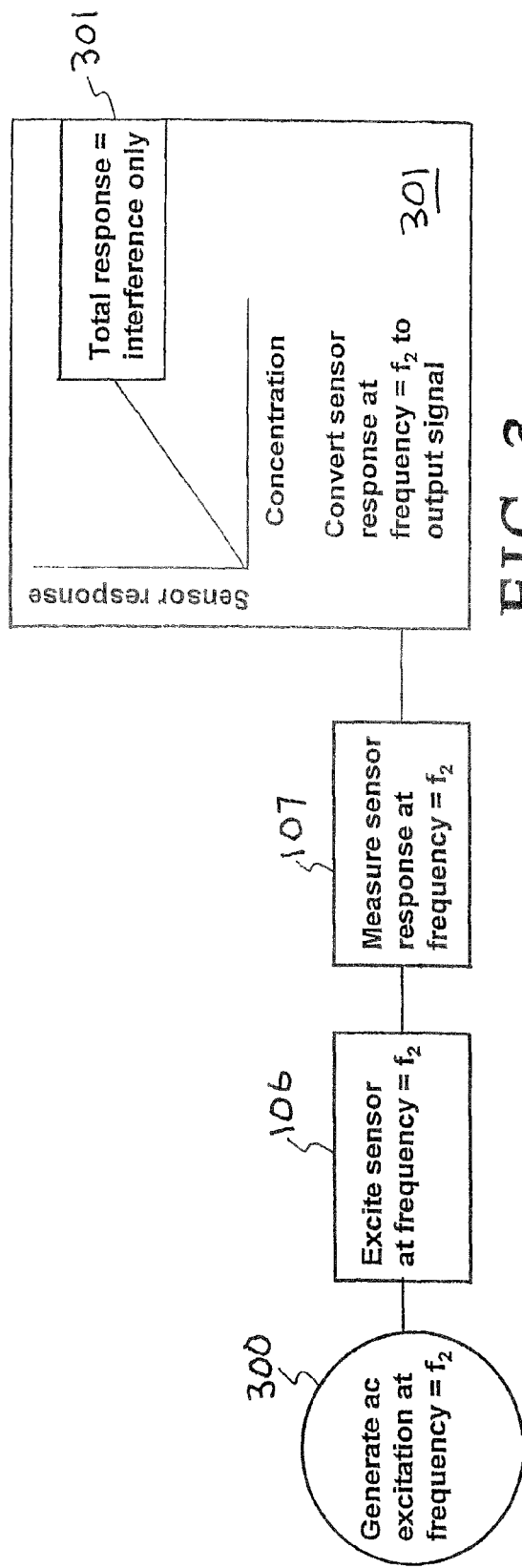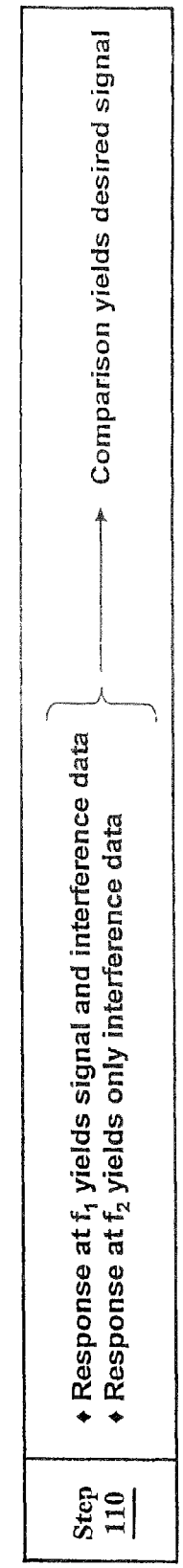

MULTIPLE FREQUENCY METHOD FOR OPERATING ELECTROCHEMICAL SENSORS

CROSS-REFERENCE TO RELATED APPLICATIONS

This application claims the benefit of U.S. Provisional Patent Application No. 60/839,500 filed Aug. 22, 2006 and titled "Multiple Frequency Technique for Operation of Electrochemical Sensors." U.S. Provisional Patent Application No. 60/839,500 filed Aug. 22, 2006 and titled "Multiple Frequency Technique for Operation of Electrochemical Sensors" is incorporated herein by this reference.

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to electrochemical sensors and more particularly to a multiple frequency method for operating electrochemical sensors.

2. State of Technology

The article, "Impedancemetric NOx Sensing Using YSZ Electrolyte and YSZ/Cr2O3 Composite Electrodes," by L. Peter Martin, Leta Y. Woo, and Robert S. Glass, in *Journal of The Electrochemical Society*, 154 (3) J97-J104 (2007), provides the following state of technology information, "Increasingly stringent emissions regulations require the development of advanced gas sensors for a variety of applications. For example, compact, inexpensive sensors are needed for detection of regulated pollutants, including hydrocarbons (HC), CO, and NOx, in automotive exhaust. Because many emerging applications, particularly monitoring of automotive exhaust, involve operation in harsh environments, which can include high temperature and corrosive or chemically reactive conditions, ceramic oxide-based electrochemical sensors have received considerable interest."

U.S. Pat. No. 6,551,149 issued Apr. 23, 2003 to Yunzhi Gao et al for measuring NOx concentration provides the following state of technology information, "Emissions of NOx from internal combustion engines used mainly in automotive vehicles and from the combustion equipment of thermal power stations and plants are a cause of photochemical smog and acid rain, are harmful to the human respiratory system and represent a major source of global environmental pollution. For these reasons the detection of noxious gases such as NOx is a major concern and a gas sensor that contributes to a reduction in the size and cost of measurement equipment and that is usable in a variety of environments has been sought. In recent years much attention has been focused on all solid-state NOx sensors inserted directly into the exhaust gas of an automotive vehicle to sense the gases continuously, and results of related research have been reported."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a multiple frequency method for the operation of a sensor. The present invention is a multiple frequency method for the operation of a sensor to measure a parameter of interest using calibration information wherein interfering parameters may be present. The method includes the steps of exciting the sensor at a first frequency providing a first sensor response, exciting the sensor at a second frequency providing a second sensor response, using the second sensor response at the second frequency and the calibration information to produce a calculated concentration of the interfering parameters, using the first sensor response at the first frequency, the calculated concentration of the interfering parameters, and the calibration information to measure the parameter of interest. The method has advantages over more traditional potentiometric (open circuit) or amperometric (dc-biased) sensors.

In one embodiment the present invention utilizes an alternating current (ac) signal across the electrodes of an electrochemical cell, and measurement of the impedance characteristics associated with the cell at the frequency of the ac signal, in particular the phase difference between the excitation signal and the sensor response at the excitation frequency. Multiple frequencies may be used, simultaneously or sequentially, to provide real-time compensation for aging, interfering species, and environmental variations (i.e., temperature). Another embodiment of the present invention is focused on sensing NOx gas in high temperature automotive exhaust gas using a solid state cell composed of a ceramic electrolyte and electrodes.

The present invention is not specific to any particular electrolyte or electrode materials, or to any particular species being sensed. The sensing methodology should be broadly applicable to the use of electrochemical cells for detecting species of interest. It does appear that the physical mechanisms resulting in the sensor response to the analyte of interest and to any interfering species or effect must be sufficiently different as to cause them to have different frequency dependencies.

The present invention has many uses. For example, the present invention can be used for the detection of pollutant gasses in a hot, flowing gas stream. Applications include the monitoring of industrial exhaust gasses and vehicle emissions. Broader applications include any application where electrochemical sensors are of interest.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

FIG. 3 shows additional details of steps of the multiple frequency method for the operation of a sensor of the present invention.

FIG. 4 illustrates the final step of the multiple frequency method for the operation of a sensor of the present invention.

DETAILED DESCRIPTION OF THE INVENTION

Figure 1:
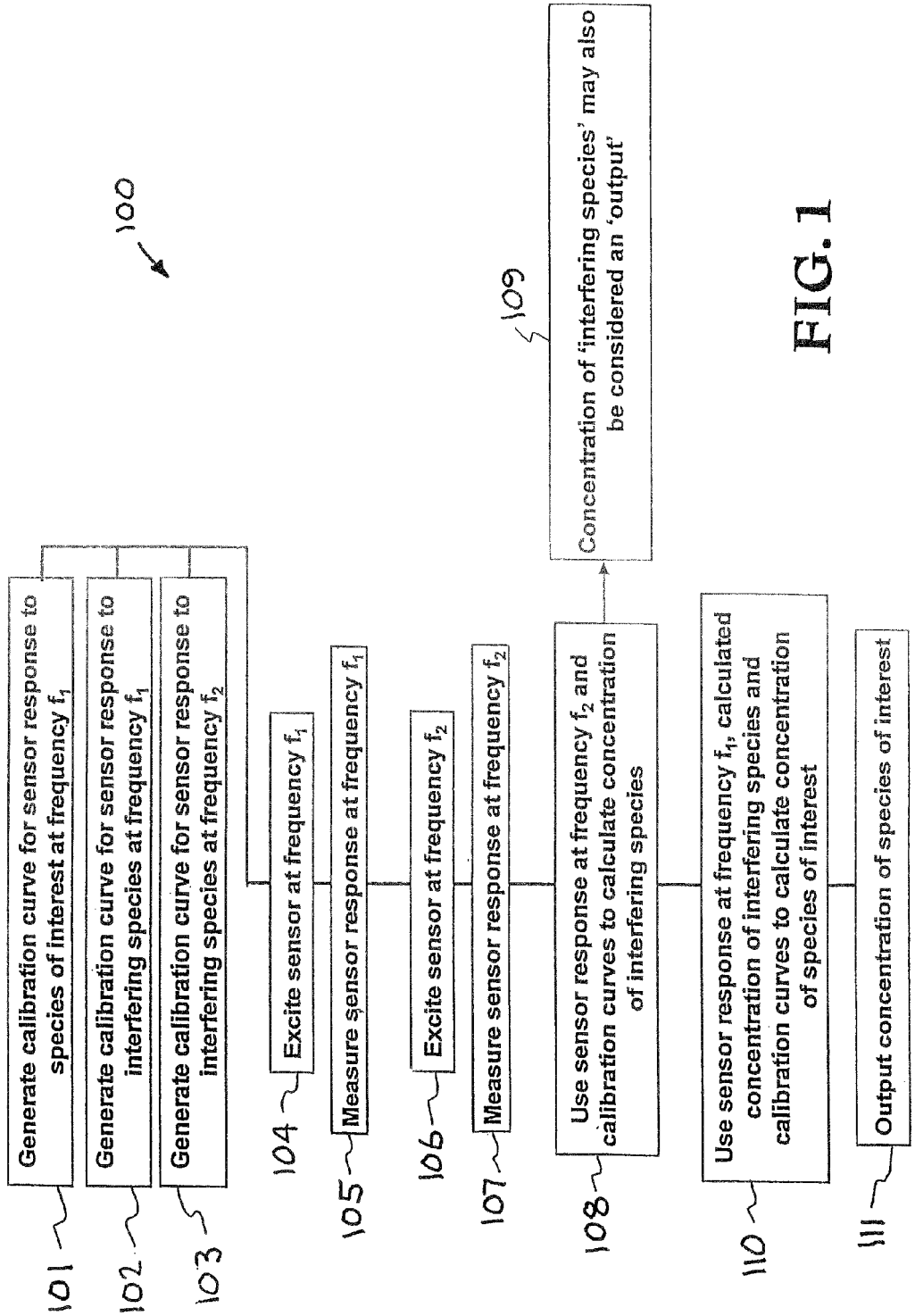
FIG. 1 illustrates an embodiment of the multiple frequency method for the operation of a sensor of the present invention.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

The present invention provides a mode of operation of sensors, particularly electrochemical sensors. The method includes the steps of exciting the sensor at a first frequency providing a first sensor response, exciting the sensor at a second frequency providing a second sensor response, using the second sensor response at the second frequency and the calibration information to produce a calculated concentration of the interfering parameters, using the first sensor response at the first frequency, the calculated concentration of the interfering parameters, and the calibration information to measure the parameter of interest. Additional information about the present invention is included in the article, "Impedancemetric NOx Sensing Using YSZ Electrolyte and YSZ/Cr203 Composite Electrodes," by L. Peter Martin, Leta Y. Woo, and Robert S. Glass, in Journal of The Electrochemical Society, 154 (3) J97-J104 (2007). The article, "Impedancemetric NOx Sensing Using YSZ Electrolyte and YSZ/Cr203 Composite Electrodes," by L. Peter Martin, Leta Y. Woo, and Robert S. Glass, in Journal of The Electrochemical Society, 154 (3) J97-J104 (2007) is incorporated in this application by this reference. United States Provisional Patent Application No. 60/839,500 filed Aug. 22, 2006 titled "Multiple Frequency Technique for Operation of Electrochemical Sensors" was incorporated into this application by reference and included the additional details. The strong effect of NO, on the complex impedance can be used as a sensing signal for the detection of NO. However, as pointed out by others, direct application of the complex impedance to sensing would require drawing the Nyquist plot and extracting the desired measurement by computer. The capability to monitor the $NO_x$ response, via the 0, of this electrochemical cell at frequencies significantly higher than 1 Hz has significant implications for 'real-world' sensor applications. Increased operating frequency typically presents the opportunity for improved signal processing (i.e., noise correction), faster sensor response, and reduced sampling time (time between measurements). This presents an additional opportunity to implement a multiple-frequency mode of operation to allow for compensation from interfering effects such as fluctuating $O_2$ concentration and variations in temperature. The data presented in the next section will demonstrate how sensor operation at two distinct frequencies can be utilized to correct for wide variations in the 02 concentration while maintaining high sensitivity to $NO_x$. A sensing frequency of 10 Hz was selected as a compromise between increased sensitivity (lower frequency) and reduced sampling time/improved signal-to-noise (higher frequency). This represents potentially an order of magnitude faster sampling rate than previous reports, while maintaining the capability to resolve sub-10 ppm levels of $NO_R$.

One embodiment of the present invention provides solid (ceramic oxide based) sensors for detection of small concentrations (ppm levels) of pollutant gasses in automotive exhaust. However, it is to be understood that applications for the invention may be significantly broader, and this application is not limited to gas sensors, or solid oxide sensors.

Another embodiment of the present invention provides an electrochemical cell consisting of an electrolyte and two (or possibly more) electrodes. The sensor is operated by applying an excitation signal which consists of a varying (typically sinusoidal) voltage difference between the two electrodes. The excitation signal consists of a fixed frequency, for example 10 Hz. A phase meter, phase lock loop, or other electronic measuring circuit is used to measure the changes in amplitude and phase of the excitation signal, after it interacts with the sensor, relative to a fixed, reference signal of the same frequency. The sensor response, which can be correlated with the impedance |Z| or the phase, is sensitive to the changes which the sensor is trying to detect (for example the $NO_x$ concentration in an exhaust gas) as well as to changes in some interfering species or effect ($O_2$ or temperature). To correct for the uncertainty introduced by the unknown effect of the interference on the sensor response, the sensor is excited at a second frequency, for example 1000 Hz, where the response is only sensitive to the interfering species or effect. Comparison of the two responses, in conjunction with the appropriate calibration information, allows calculation of the concentration of the species of interest (i.e., NO) and of the interfering species.

One aspect of the present invention is the operation at non-zero (ac) frequency. Electrochemical gas sensors are traditionally operated either passively (no excitation at all) or using a zero-frequency (dc) excitation. Operating at non-zero frequency provides several advantages over the traditional dc modes of operation. There is more 'information' in the ac response because it is, by definition, a dynamic (non-steady state) response and therefore contains not only amplitude information, but also some measure of the time-dependence of the response. Also, the frequency determines response and sampling times (with 1/frequency representing a general limitation for the sampling rate). Thus, it is desirable to operate at the highest frequency at which sufficient sensitivity can be obtained. Additionally, the sensor response to different species (say $O_2$ and NO) often can be distinguished by virtue of the differences in the frequency dependence of the responses to the different species. This is not possible using the traditional dc approach. This provides a third point of novelty of the proposed sensor . . . that the sensor can be simultaneously operated at two (or more) widely different frequencies to provide a compensation for these interfering effects. That is, for example, at 10 Hz the sensor senses both changes in the concentrations of NOx and O2, while at 1000 Hz it senses only the changes in $O_2$. Thus, by comparing these signals the competing effects of variations of several percent in the $O_2$ background can be deconvolved from the effects of ppm changes in the $NO_x$ concentration.

One embodiment of the present invention includes the intentional use of a high impedance cell to maximize the sensor response. This is a complicated issue but can be stated that the high impedance forces the sensor to be limited (kinetically) by the redox reactions at the interfaces. Since this is where the sensing reaction is generally thought to occur, the net result is that the sensing response dominates the sensor behavior, and thus makes it a good sensor. Another embodiment of the present invention includes the use of an ac excitation for the sensor at frequencies above ~1 Hz. In particular, the use of the phase response of the sensor as the metric which is correlated with the gas composition. Another embodiment of the present invention includes the use of multiple frequencies to compensate for interfering gasses and or environmental variations. As an example, the target application of the ongoing project is to detect 2-25 ppm NO in a background of 5-20% $O_2$. At low frequencies, <40 Hz, the sensors we have fabricated are sensitive to both the NO and $O_2$ concentrations. However, at higher frequencies, >500 Hz, the sensor is only sensitive to $O_2$. By measuring at both frequencies, we can compensate the effect of large variations (several %) in the oxygen concentration in a way that allows us to clearly resolve changes in the NO concentrations on the ppm level.

Method for the Operation of a Sensor

Referring now to the drawings and in particular to FIG. 1, an embodiment of the multiple frequency method for the operation of a sensor of the present invention is illustrated. This embodiment of the multiple frequency method for the operation of a sensor of the present invention is designated generally by the reference numeral 100. The method 100 is a multiple frequency method for the operation of a sensor to measure a parameter of interest using calibration information, wherein interfering parameters may be present. The method 100 includes the steps of exciting the sensor at a first frequency providing a first sensor response, exciting the sensor at a second frequency providing a second sensor response, using the second sensor response at the second frequency and the calibration information to produce a calculated concentration of the interfering parameters, using the first sensor response at the first frequency, the calculated concentration of the interfering parameters, and the calibration information to measure the parameter of interest.

The method 100 is an embodiment of the multiple frequency method for the operation of a general sensor trying to measure 1 species of interest with correction for 1 interfering species. The actual sensing element is designed so that the relative sensitivities to the two species are different at two different frequencies—$f_1$ and $f_2$. Step 101 is to generate a calibration curve for sensor response to species of interest at frequency $f_1$. Step 102 is to generate a calibration curve for sensor response to interfering species at frequency $f_1$. Step 103 is to generate a calibration curve for sensor response to interfering species at frequency $f_2$. Steps 101, 102, and 103 are performed once, prior to sensor operation.

Step 104 is to excite the sensor at frequency $f_1$. Response at $f_1$ contains contributions from both species of interest and interfering species. Step 105 is to measure sensor response at frequency $f_1$. Step 106 is to excite the sensor at frequency $f_2$. Step 107 is to measure sensor response at frequency $f_2$. Response at $f_2$ contains contributions only from interfering species.

Step 108 is to use sensor response at frequency $f_2$ and calibration curves to calculate concentration of interfering species. In Step 109 concentration of 'interfering species' may also be considered an 'output.'

Step 110 is to use sensor response at frequency $f_1$, calculated concentration of interfering species and calibration curves to calculate concentration of species of interest. Step 111 provides output concentration of species of interest.

The method 100 illustrated in FIG. 1 is a computer implemented multiple frequency method for the operation of a sensor to measure a parameter of interest using calibration curves, wherein interfering parameters may be present. The method 100 illustrated in FIG. 1 includes the step 104 of exciting the sensor at a first frequency providing a first sensor response recorded on a computer-readable medium, the step 106 exciting the sensor at a second frequency providing a second sensor response recorded on a computer-readable medium, the step 108 using said second sensor response at said second frequency and the calibration information to produce a calculated concentration of the interfering parameters recorded on a computer-readable medium, and the step 110 using said first sensor response at said first frequency, said calculated concentration of the interfering parameters, and the calibration information to measure the parameter of interest.

Figure 2:
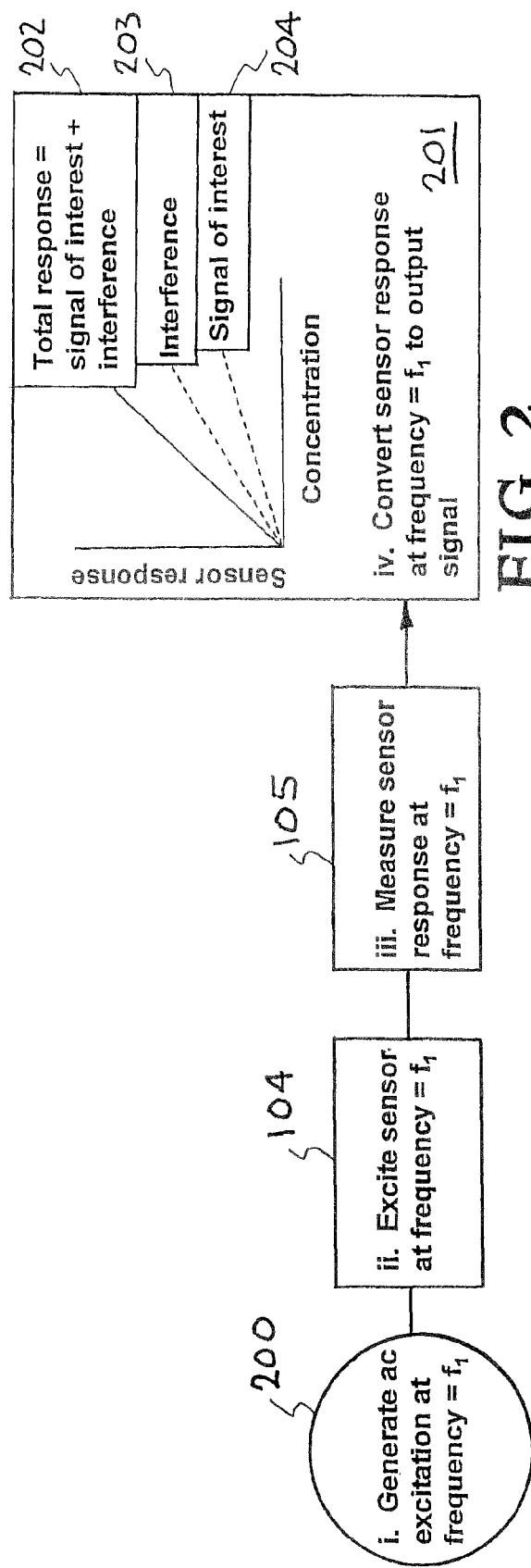
FIG. 2 shows additional details of steps of the multiple frequency method for the operation of a sensor of the present invention.

Referring now to FIG. 2, additional details of Steps 104 and 105 are illustrated. The method 100 includes the step 104 of exciting the sensor at a first frequency providing a first sensor response recorded on a computer-readable medium and step 105 of measure sensor response at frequency $f_1$ and recorded it on a computer-readable medium. Step 104 is to excite the sensor at frequency $f_1$. This is accomplished by the step 200 generate ac excitation at frequency=$f_1$. Step 105 is to measure sensor response at frequency $f_1$. Step 201 includes convert sensor response at frequency=$f_1$ to output signal. This is illustrated by the plot of "Sensor Response" vs. "Concentration." This produces the lines 202 "Total response=signal of interest+interference," the line 203 "Interference," and line 204 "Signal of interest." Response is strong, but sensitivity to interference is high. Interference could come from any source that affects sensor output (concentration of other gasses, temperature, etc.).

Referring now to FIG. 3, additional details of Steps 106 and 107 are illustrated. Step 106 is to excite the sensor at frequency $f_2$. This includes step 300 generate ac excitation at frequency=$f_2$. Step 107 is to measure sensor response at frequency $f_2$. Response is negligible, but sensitivity to interference is still high. Response at $f_2$ contains contributions only from interfering species. The method 100 includes the step 106 exciting the sensor at a second frequency providing a second sensor response recorded on a computer-readable medium. Step 107 is to measure sensor response at frequency $f_2$ and record it on a computer-readable medium. This includes step 301 convert sensor response at frequency=$f_2$ to output signal. This is illustrated by the plot of "Sensor Response" vs. "Concentration." This produces the line 301 "Total response interference only."

Referring now to FIG. 4, the final step of using the first sensor response at the first frequency, the calculated concentration of the interfering parameters, and the calibration information to measure the parameter of interest is illustrated. This step is to calculate signal of interest from the responses at the two frequencies. The response at $f_1$ yields signal and interference data and the response at $f_2$ yields only interference data. A comparison yields the desired signal.

Method for the Operation of a NO Sensor in a Background of Varying $O_2$

Figure 5:
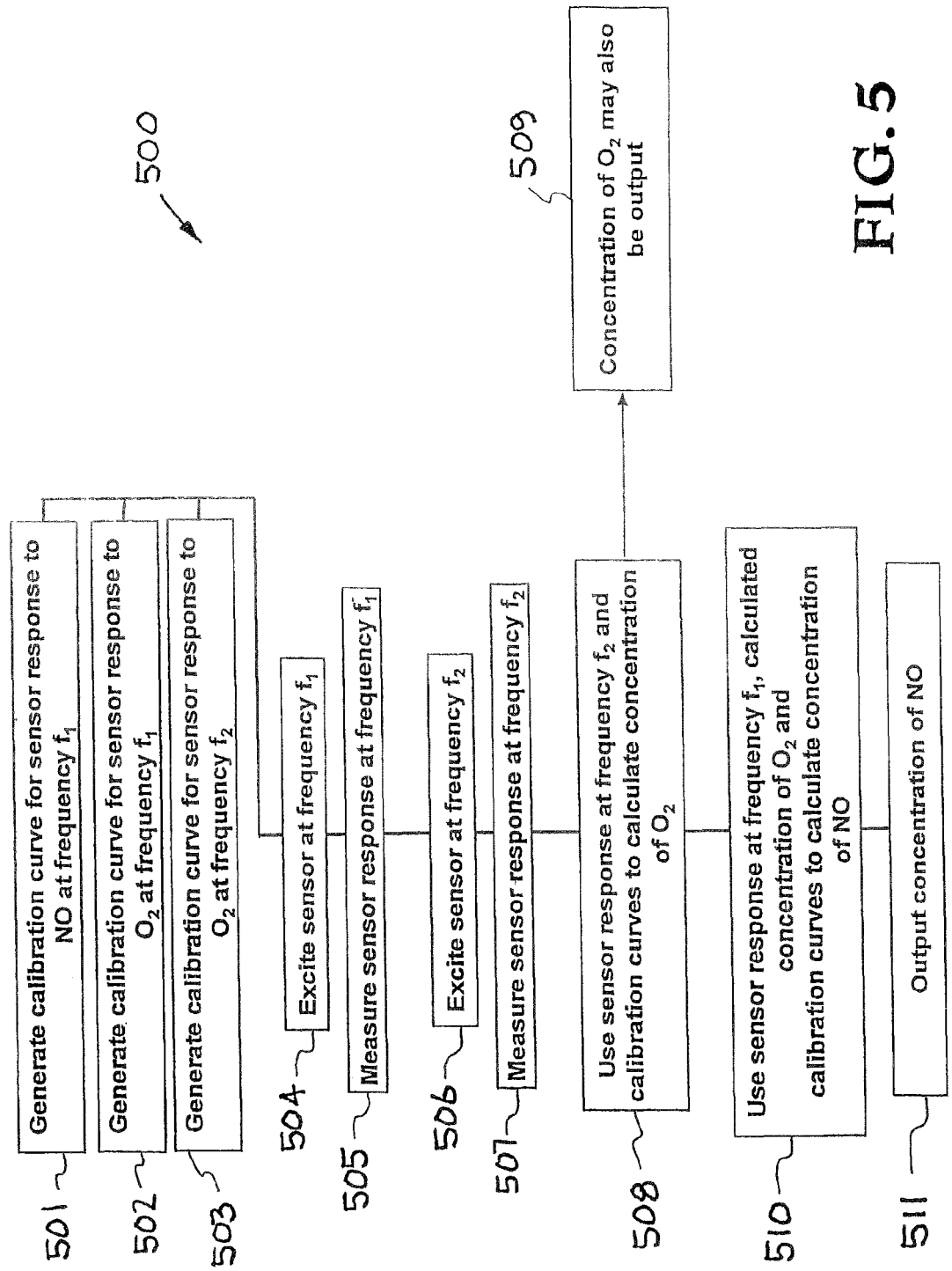
FIG. 5 illustrates another embodiment of the multiple frequency method for the operation of a sensor of the present invention to detect NO in a varying $O_2$ background.

Referring now to the drawings and in particular to FIG. 5, an embodiment of the multiple frequency method for the operation of a NO sensor of the present invention trying to measure the concentration of NO in a background with varying $O_2$ concentration is illustrated. The actual sensing element must be designed so that the relative sensitivities to NO and $O_2$ are different at two different frequencies—$f_1$ and $f_2$. This embodiment of the multiple frequency method for the operation of a NO sensor of the present invention is designated generally by the reference numeral 500. The method 500 is a multiple frequency method for the operation of a NO sensor to measure a parameter of interest using calibration information, wherein interfering Varying $O_2$ may be present.

The method 500 includes the steps of exciting the NO sensor at a first frequency providing a first NO sensor response to both NO and $O_2$, exciting the NO sensor at a second frequency providing a second sensor response to only $O_2$, using the second sensor response at the second frequency and the calibration information to produce a calculated concentration of $O_2$, using the first NO sensor response at the first frequency, the calculated concentration of $O_2$, and the calibration information to calculate the NO concentration.

The method 500 is an embodiment of the multiple frequency method for the operation of a NO sensor trying to measure the concentration of NO in a background with varying $O_2$ concentration. The actual sensing element must be designed so that the relative sensitivities to NO and $O_2$ are different at two different frequencies—$f_1$ and $f_2$. Step 501 is to generate a calibration curve for sensor response to NO at frequency $f_1$. Step 502 is to generate a calibration curve for sensor response to $O_2$ at frequency $f_1$. Step 503 is to generate a calibration curve for sensor response to $O_2$ at frequency $f_2$. Steps 501, 502, and 503 are performed once, prior to NO sensor operation a (i.e., prior to placing the sensor 'in service').

Step 504 is to excite the NO sensor at frequency $f_1$. Response at $f_1$ contains contributions from both species of interest and interfering species (NO and $O_2$). Step 505 is to measure NO sensor response at frequency $f_1$. Step 506 is to excite the NO sensor at frequency $f_2$. Step 507 is to measure NO sensor response at frequency $f_2$. Response at $f_2$ contains contributions only from the interfering species $O_2$.

Step 508 is to use NO sensor response at frequency $f_2$ and calibration curves to calculate concentration of interfering species $O_2$. In Step 509 concentration of 'interfering species $O_2$' may also be considered an 'output.'

Step 510 is to use NO sensor response at frequency $f_1$, calculated concentration of interfering species $O_2$ and calibration curves to calculate concentration of species of interest NO. Step 511 provides output concentration of species of interest NO.

The method 500 illustrated in FIG. 5 is a computer implemented multiple frequency method for the operation of a NO sensor to measure a parameter of interest using calibration curves, wherein interfering parameters may be present. The method 500 illustrated in FIG. 5 includes the step 504 of exciting the NO sensor at a first frequency providing a first NO sensor response from both species of interest and interfering species (NO and $O_2$) recorded on a computer-readable medium, the step 506 exciting the NO sensor at a second frequency providing a second NO sensor response to $O_2$ recorded on a computer-readable medium, the step 508 using said second NO sensor response at said second frequency for the interfering species ($O_2$) and the calibration information to produce a calculated concentration of the interfering parameter $O_2$ recorded on a computer-readable medium, and the step 510 using said first NO sensor response at said first frequency, said calculated concentration of the interfering parameters $O_2$, and the calibration information to calculate the parameter of interest NO.

EXAMPLE

NO Sensor in a Background of Varying $O_2$

An example of the multiple frequency method for the operation of a NO sensor of the present invention trying to measure the concentration of NO in a background with varying $O_2$ concentration is provided to further explain the principles of the invention. As illustrated in FIG. 5, a calibration curve for sensor response to NO at frequency $f_1$ is produced to provide calibration information. A calibration curve for sensor response to $O_2$ at frequency $f_1$ is produced to provide calibration information. A calibration curve for sensor response to $O_2$ at frequency $f_2$ is produced to provide calibration information.

In Step 504 the NO sensor was excited at frequency $f_1$ of 10 Hz. The response at $f_1$ contains contributions from both NO and $O_2$.

In Step 505 the NO sensor phase response at frequency $f_1$ was measured as −40.5 degrees.

In Step 506 the NO sensor was excited at frequency $f_2$ of 1000 Hz.

In Step 507 the NO sensor response at frequency $f_2$ was measured as −32.3 degrees. Response at $f_2$ contains contributions only from $O_2$.

In Step 508 the NO sensor response at frequency $f_2$ and calibration curves were used to calculate concentration of interfering species $O_2$ as 7.0%.

In Step 510 the NO sensor response at frequency $f_1$, calculated concentration of interfering species $O_2$, and calibration curves were used to calculate concentration of species of interest NO as 15 ppm.

The concentration of species of interest NO 15 ppm is the output as shown in Step 511.

Note: in Step 509 the concentration of "interfering species $O_2$ 7.0%" may also be considered an "output."

Figure 6:
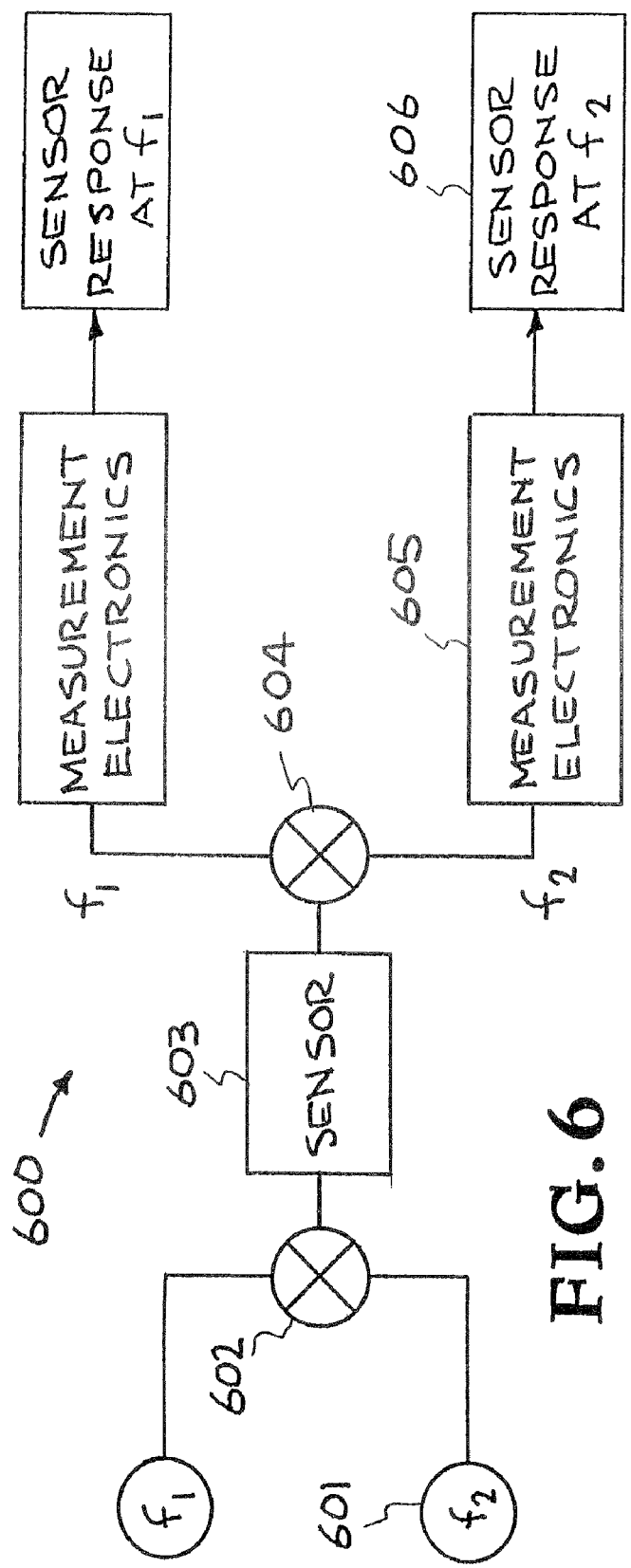
FIG. 6 illustrates an alternate embodiment of the invention where frequencies $f_1$ and $f_2$ are excited simultaneously.

Referring now to FIG. 6, an alternate embodiment of the invention is illustrated wherein frequencies $f_1$ and $f_2$ are excited simultaneously. The alternate embodiment is designated generally the reference numeral 600. The method 600 includes the following steps. In step 601 excitation signals at frequencies $f_1$ and $f_2$ are generated. In step 602, the excitation signals are electronically mixed (added) together to produce a single excitation signal with two frequency components at $f_1$ and $f_2$. In step 603 the sensor is excited by the combined signal. In step 604, the sensor response is electronically separated into the frequency components at $f_1$ and $f_2$. In step 605, measurement electronics are used to measure the sensor response at $f_1$ and $f_2$. These responses are then passed (step 606) to a computer for further analysis.

Figure 7:
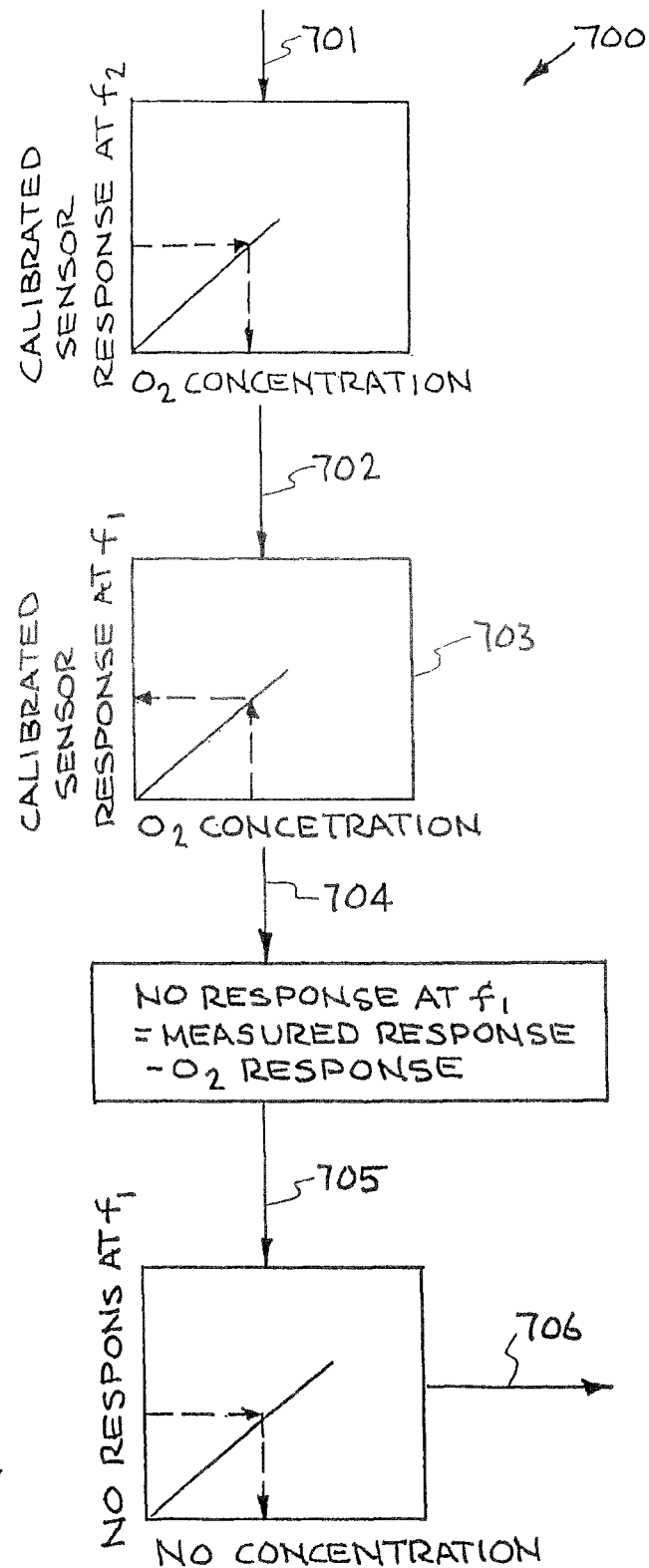
FIG. 7 illustrates schematically the process of determining the NO concentration by using the multiple frequency technique to correct for an unknown $O_2$ concentration.

Referring now to FIG. 7, the process of determining the NO concentration by using the multiple frequency technique to correct for an unknown $O_2$ concentration is illustrated. The process is designated generally by the reference numeral 700. Note that in this example the sensor has been configured so that the response at $f_1$ is sensitive to both NO and $O_2$ concentrations, while the response at $f_2$ is sensitive only to the $O_2$ concentration. The process 700 begins with the measured sensor response at $f_1$ and $f_2$. These responses may be measured via simultaneous excitation at the two frequencies, as described in FIG. 6, or via consecutive excitations at each frequency (i.e., $f_1$ then $f_2$). The process of determining the NO concentration in FIG. 7 consists of the following steps. In step 701 the measured sensor response at $f_2$ is read from the computer. In step 702, a predetermined calibration curve is used to determine the $O_2$ concentration from the measured sensor response at $f_2$. In step 703 the $O_2$ concentration determined from the $f_2$ response is used to predict the portion of the sensor response at $f_1$ that corresponds only to the contribution of the $O_2$ concentration. This is accomplished using a $2^{nd}$, predetermined calibration curve. In step 704 the portion of the sensor response at $f_1$ due to the NO concentration is determined from the total measured response and the $O_2$ response calculated in step 703. In step 705 a $3^{rd}$ predetermined calibration curve is used to determine the NO concentration from the NO response determined in step 704. Finally, in step 706 the NO concentration is output from the measurement system.

Method for the Operation of a CO Sensor in a Background Varying $O_2$

Figure 8:
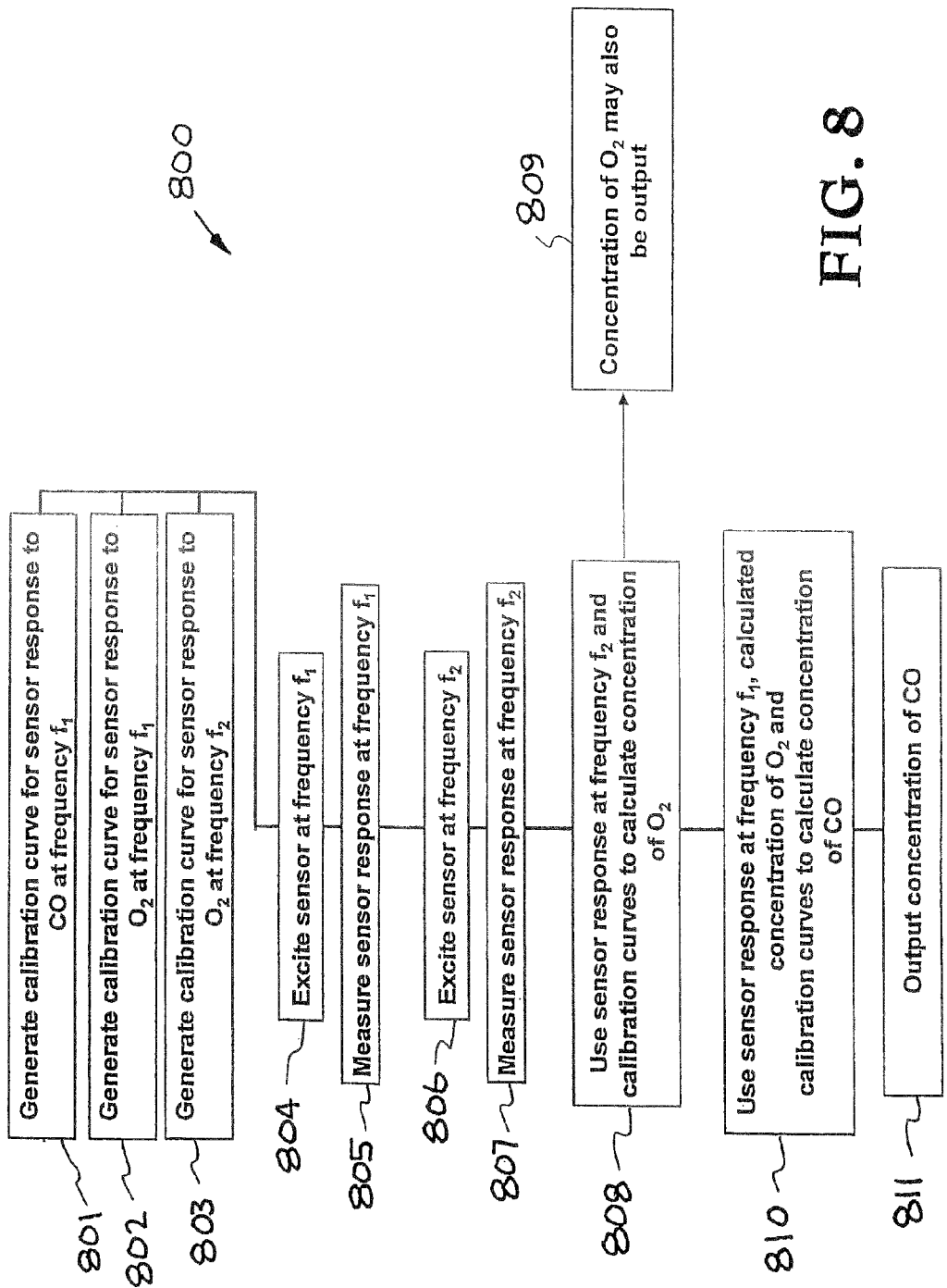
FIG. 8 illustrates another embodiment of the multiple frequency method for the operation of a sensor of the present invention to detect CO in a varying $O_2$ background.

Referring now to the drawings and in particular to FIG. 8, an embodiment of the multiple frequency method for the operation of a CO sensor of the present invention trying to measure the concentration of CO in a background with varying $O_2$ concentration is illustrated. The actual sensing element must be designed so that the relative sensitivities to CO and $O_2$ are different at two different frequencies—$f_1$ and $f_2$. This embodiment of the multiple frequency method for the operation of a CO sensor of the present invention is designated generally by the reference numeral 800. The method 800 is a multiple frequency method for the operation of a CO sensor to measure a parameter of interest using calibration information, wherein interfering varying $O_2$ may be present.

The method 800 includes the steps of exciting the CO sensor at a first frequency providing a first CO sensor response at $f_1$ that contains contributions from both CO and $O_2$, exciting the CO sensor at a second frequency providing a second sensor response at $f_2$ that contains contributions only from $O_2$, using the first sensor response of both CO and $O_2$ at $f_1$ and the calibration information to produce a calculated concentration of $O_2$, using the first CO sensor response at the first frequency, the calculated concentration of $O_2$, and the calibration information to measure CO.

Step 801 is to generate a calibration curve for sensor response to CO at frequency $f_1$. Step 802 is to generate a calibration curve for sensor response to $O_2$ at frequency $f_1$. Step 803 is to generate a calibration curve for sensor response to $O_2$ at frequency $f_2$. Steps 801, 802, and 803 are performed once, prior to CO sensor operation.

Step 804 is to excite the CO sensor at frequency $f_1$. Response at $f_1$ contains contributions from both CO and $O_2$. Step 805 is to measure CO sensor response at frequency $f_1$. Step 806 is to excite the CO sensor at frequency $f_2$.

Step 807 is to measure CO sensor response at frequency $f_2$. Response at $f_2$ contains contributions only from $O_2$.

Step 808 is to use CO sensor response at frequency $f_2$ and calibration curves to calculate concentration of $O_2$. In Step 809 concentration of '$O_2$' may be considered an 'output.'

Step 810 is to use CO sensor response at frequency $f_1$, calculated concentration of $O_2$ and calibration information to calculate concentration of CO. Step 811 provides output concentration of species of interest CO.

The method 800 illustrated in FIG. 8 is a computer implemented multiple frequency method for the operation of a CO sensor to measure a parameter of interest using calibration curves, wherein interfering parameters may be present. The method 800 illustrated in FIG. 8 includes the step 804 of exciting the CO sensor at a first frequency providing a first CO sensor response from both species of interest and interfering species (CO and $O_2$) recorded on a computer-readable medium, the step 806 exciting the CO sensor at a second frequency providing a second CO sensor response recorded on a computer-readable medium, the step 808 using said second CO sensor response at said second frequency from both species of interest and interfering species (CO and $O_2$) and the calibration information to produce a calculated concentration of the interfering parameters $O_2$ recorded on a computer-readable medium, and the step 810 using said first CO sensor response at said first frequency, said calculated concentration of the interfering parameters $O_2$, and the calibration information to measure the parameter of interest CO.

Method for the Operation of a NO Sensor with Uncertain Temperature

Figure 9:
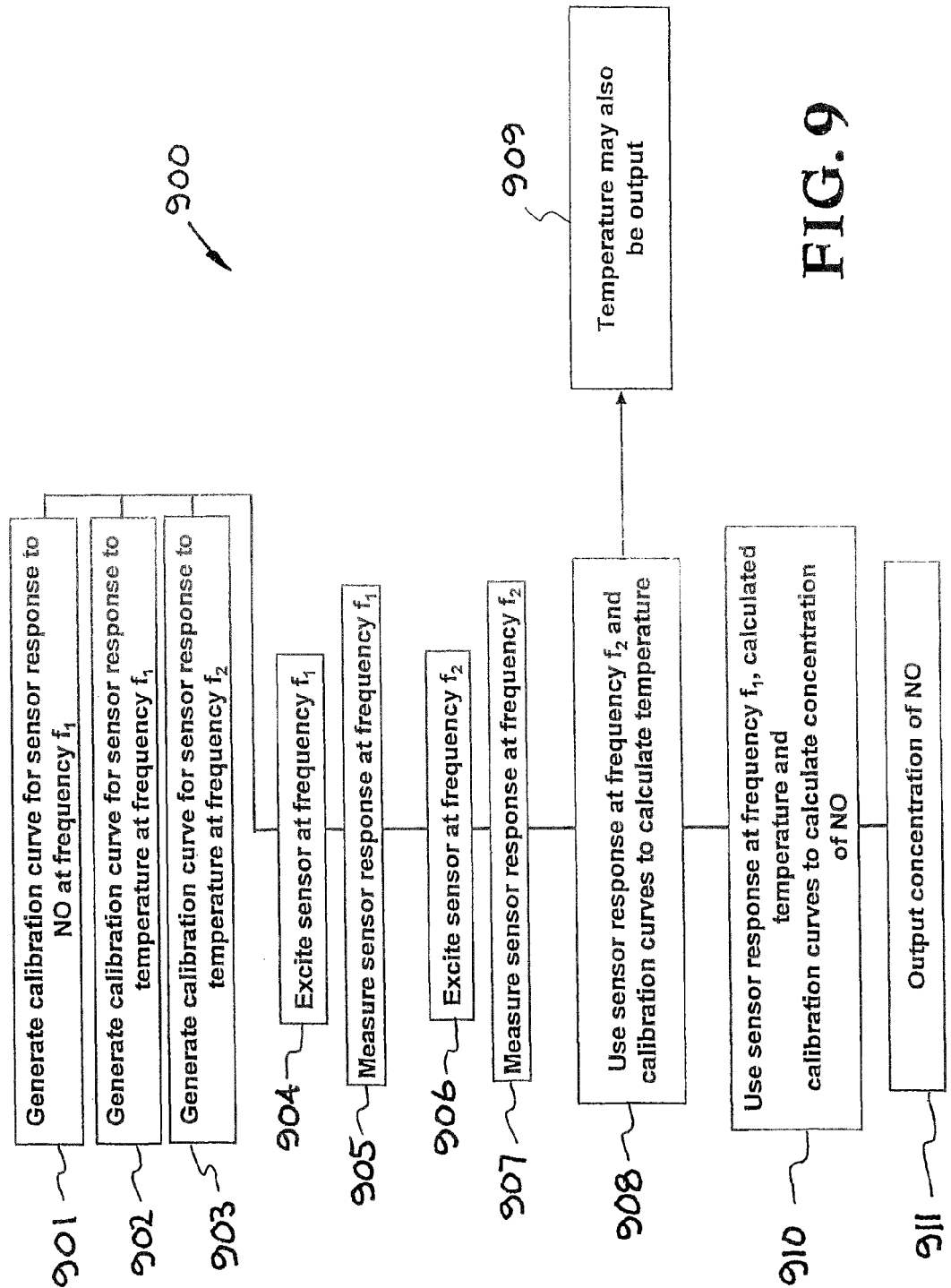
FIG. 9 illustrates yet another embodiment of the multiple frequency method for the operation of a sensor of the present invention to detect NO in a varying temperature environment.

Referring now to the drawings and in particular to FIG. 9, an embodiment of the multiple frequency method for the operation of a NO sensor of the present invention trying to measure the concentration of NO where the temperature is uncertain is illustrated. The actual sensing element must be designed so that the relative sensitivities to NO and temperature are different at two different frequencies—$f_1$ and $f_2$. This embodiment of the multiple frequency method for the operation of a NO sensor of the present invention is designated generally by the reference numeral 900. The method 900 is a multiple frequency method for the operation of a NO sensor to measure a parameter of interest using calibration information, wherein interfering varying temperature may occur.

The method 900 includes the steps of exciting the NO sensor at a first frequency providing a first NO sensor response at $f_1$ that contains contributions from both NO and temperature, exciting the NO sensor at a second frequency providing a second sensor response at $f_2$ that contains contributions only from temperature, using the first sensor response of both NO and temperature at $f_1$ and the calibration information to produce a calculated temperature, using the first NO sensor response at the first frequency, the calculated temperature, and the calibration information to measure NO.

The method 900 is an embodiment of the multiple frequency method for the operation of a NO sensor trying to measure the concentration of NO with uncertain temperature. The actual sensing element must be designed so that the relative sensitivities to NO and temperature are different at two different frequencies—$f_1$ and $f_2$. Step 901 is to generate a calibration curve for sensor response to NO at frequency $f_1$. Step 902 is to generate a calibration curve for sensor response to temperature at frequency $f_1$. Step 903 is to generate a calibration curve for sensor response to temperature at frequency $f_2$. Steps 901, 902, and 903 are performed once, prior to NO sensor operation.

Step 904 is to excite the NO sensor at frequency $f_1$. Response at $f_1$ contains contributions from both NO and temperature. Step 905 is to measure NO sensor response at frequency $f_1$. Step 906 is to excite the NO sensor at frequency $f_2$.

Step 907 is to measure NO sensor response at frequency $f_2$. Response at $f_2$ contains contributions only from temperature Step 908 is to use NO sensor response at frequency $f_2$ and calibration curves to calculate temperature. In Step 909 "temperature" may be considered an "output."

Step 910 is to use NO sensor response at frequency $f_1$, calculated temperature and calibration information to calculate concentration of NO. Step 911 provides output concentration of species of interest NO.

The method 900 illustrated in FIG. 9 is a computer implemented multiple frequency method for the operation of a NO sensor to measure a parameter of interest using calibration curves, wherein interfering parameters may be present. The method 900 illustrated in FIG. 9 includes the step 904 of exciting the NO sensor at a first frequency providing a first NO sensor response from both species of interest and interfering species (NO and temperature) recorded on a computer-readable medium, the step 906 exciting the NO sensor at a second frequency providing a second NO sensor response recorded on a computer-readable medium, the step 908 using said second NO sensor response at said second frequency from both species of interest and interfering species (NO and temperature) and the calibration information to produce a calculated temperature recorded on a computer-readable medium, and the step 910 using said first NO sensor response at said first frequency, said calculated temperature, and the calibration information to measure the parameter of interest NO.

Method for the Operation of a $H_2$ Sensor in a Background Varying $H_2O$

Figure 10:
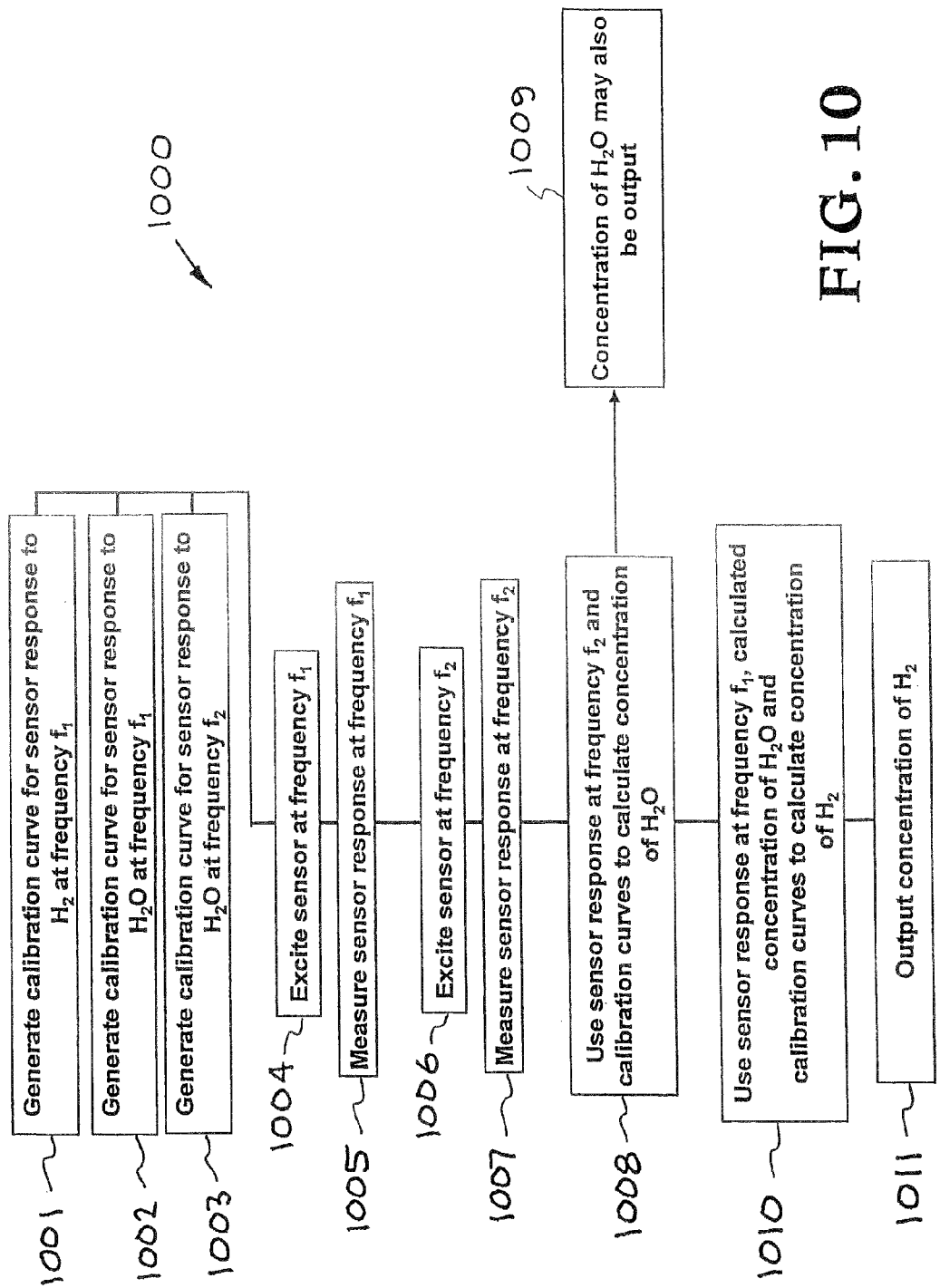
FIG. 10 illustrates the operation of a $H_2$ sensor trying to measure the concentration of $H_2$ in a background with varying $H_2O$ concentration.

Referring now to the drawings and in particular to FIG. 10, an embodiment of the multiple frequency method for the operation of a $H_2$ sensor of the present invention trying to measure the concentration of $H_2$ in a background with varying $H_2O$ concentration is illustrated. The actual sensing element must be designed so that the relative sensitivities to $H_2$ and $H_2O$ are different at two different frequencies—$f_1$ and $f_2$. This embodiment of the multiple frequency method for the operation of a $H_2$ sensor of the present invention is designated generally by the reference numeral 1000. The method 1000 is a multiple frequency method for the operation of a $H_2$ sensor to measure the $H_2$ concentration using calibration information, wherein varying $H_2O$ concentration may interfere with the sensor response.

The method 1000 includes the steps of exciting the $H_2$ sensor at a first frequency providing a first $H_2$ sensor response to both $H_2$ and $H_2O$ concentrations, exciting the $H_2$ sensor at a second frequency providing a second sensor response to $H_2O$, using the second sensor response at the second frequency and the calibration information to produce a calculated concentration of $H_2O$, using the first $H_2$ sensor response at the first frequency, the calculated concentration of $H_2O$, and the calibration information to calculate the $H^2$ concentration.

The method 1000 is an embodiment of the multiple frequency method for the operation of a $H_2$ sensor trying to measure the concentration of $H_2$ in a background with varying $H_2O$ concentration. The actual sensing element must be designed so that the relative sensitivities to $H_2$ and $H_2O$ are different at two different frequencies—$f_1$ and $f_2$. Step 1001 is to generate a calibration curve for sensor response to $H_2$ at frequency $f_1$. Step 1002 is to generate a calibration curve for sensor response to $H_2O$ at frequency $f_1$. Step 1003 is to generate a calibration curve for sensor response to $H_2O$ at frequency $f_2$. Steps 1001, 1002, and 1003 are performed once, prior to $H_2$ sensor operation.

Step 1004 is to excite the $H_2$ sensor at frequency $f_1$. Response at $f_1$ contains contributions from both species of interest and interfering species ($H_2$ and $H_2O$). Step 1005 is to measure $H_2$ sensor response at frequency $f_1$. Step 1006 is to excite the $H_2$ sensor at frequency $f_2$. Step 1007 is to measure $H_2$ sensor response at frequency $f_2$. Response at $f_2$ contains contributions only from the interfering species $H_2O$.

Step 1008 is to use $H_2$ sensor response at frequency $f_2$ and calibration curves to calculate concentration of interfering species $H_2O$. In Step 1009 concentration of 'interfering species $H_2O$' may also be considered an 'output.'

Step 1010 is to use $H_2$ sensor response at frequency $f_1$, calculated concentration of interfering species $H_2O$ and calibration curves to calculate concentration of species of interest $H_2$. Step 1011 provides output concentration of species of interest $H_2$.

The method 1000 illustrated in FIG. 10 is a computer implemented multiple frequency method for the operation of a $H_2$ sensor to measure a parameter of interest using calibration curves, wherein interfering parameters may be present. The method 1000 illustrated in FIG. 10 includes the step 1004 of exciting the $H_2$ sensor at a first frequency providing a first $H_2$ sensor response from both species of interest and interfering species ($H_2$ and $H_2O$) recorded on a computer-readable medium, the step 1006 exciting the $H_2$ sensor at a second frequency providing a second $H_2$ sensor response recorded on a computer-readable medium, the step 1008 using said second $H_2$ sensor response at said second frequency from both species of interest and interfering species ($H_2$ and $H_2O$) and the calibration information to produce a calculated concentration of the interfering parameters $H_2O$ recorded on a computer-readable medium, and the step 1010 using said first $H_2$ sensor response at said first frequency, said calculated concentration of the interfering parameters $H_2O$, and the calibration information to measure the parameter of interest $H_2$.

Method for the Operation of a $NO_2$ Sensor in a Background Varying $O_2$

Figure 11:
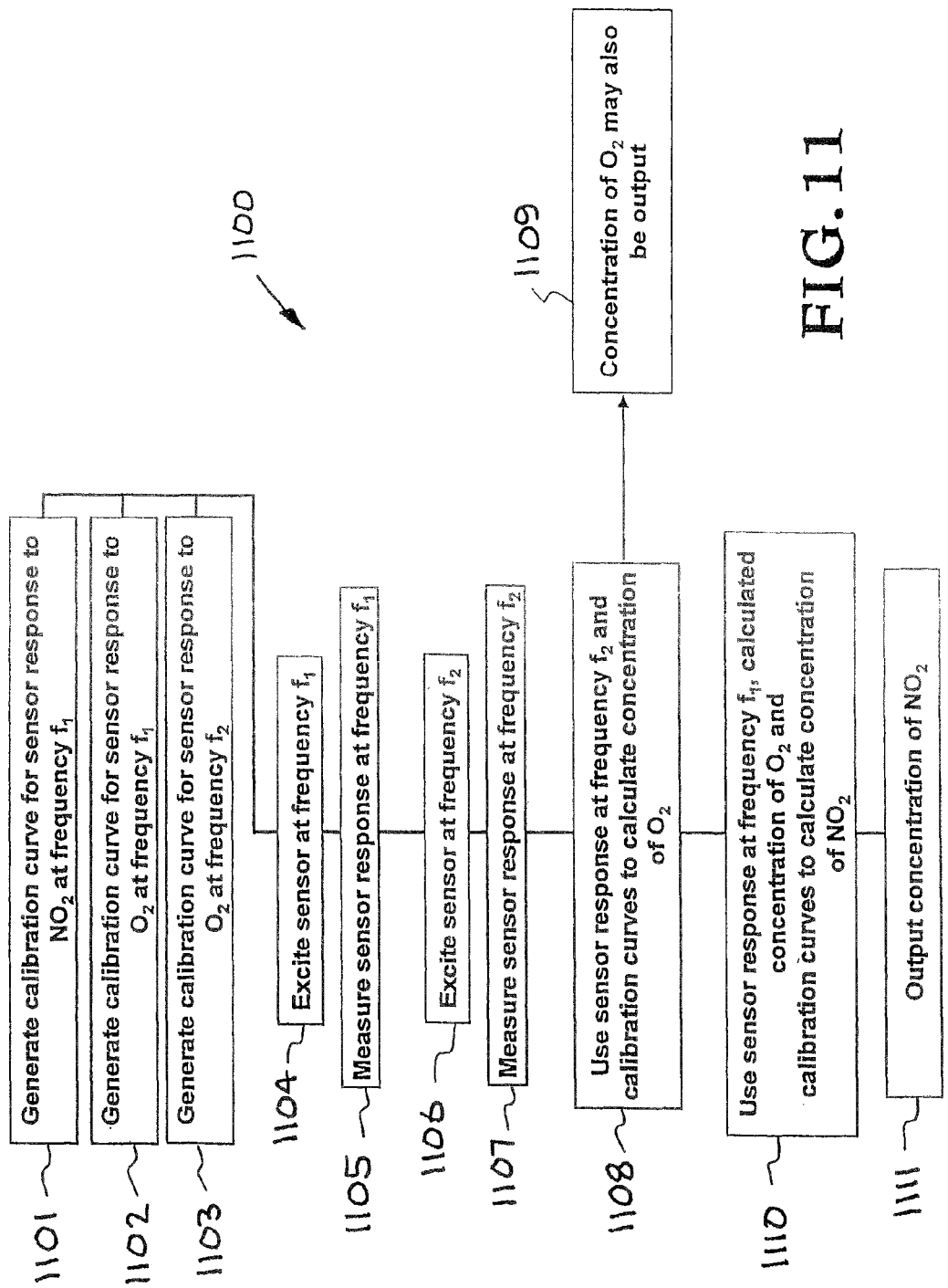
FIG. 11 illustrates the operation of a $NO_2$ sensor trying to measure the concentration of $NO_2$ in a background with varying $O_2$ concentration.

Referring now to the drawings and in particular to FIG. 11, an embodiment of the multiple frequency method for the operation of a $NO_2$ sensor of the present invention trying to measure the concentration of $NO_2$ in a background with varying $O_2$ concentration is illustrated. The actual sensing element must be designed so that the relative sensitivities to $NO_2$ and $O_2$ are different at two different frequencies—$f_1$ and $f_2$. This embodiment of the multiple frequency method for the operation of a $NO_2$ sensor of the present invention is designated generally by the reference numeral 1100. The method 1100 is a multiple frequency method for the operation of a $NO_2$ sensor to measure a parameter of interest using calibration information, wherein interfering varying $O_2$ concentration may be present.

The method 1100 includes the steps of exciting the $NO_2$ sensor at a first frequency providing a first $NO_2$ sensor response sensitive to both $NO_2$ and $O_2$, exciting the $NO_2$ sensor at a second frequency providing a second sensor response to only $O_2$, using the second sensor response at the second frequency and the calibration information to produce a calculated concentration of $O_2$, using the first $NO_2$ sensor response at the first frequency, the calculated concentration of $O_2$, and the calibration information to calculate the $NO_2$ concentration.

The method 1100 is an embodiment of the multiple frequency method for the operation of a $NO_2$ sensor trying to measure the concentration of $NO_2$ in a background with varying $O_2$ concentration. The actual sensing element must be designed so that the relative sensitivities to $NO_2$ and $O_2$ are different at two different frequencies—$f_1$ and $f_2$. Step 1101 is to generate a calibration curve for sensor response to $NO_2$ at frequency $f_1$. Step 1102 is to generate a calibration curve for sensor response to $O_2$ at frequency $f_1$. Step 1103 is to generate a calibration curve for sensor response to $O_2$ at frequency $f_2$. Steps 1101, 1102, and 1103 are performed once, prior to $NO_2$ sensor operation.

Step 1104 is to excite the $NO_2$ sensor at frequency $f_1$. Response at $f_1$ contains contributions from both species of interest and interfering species ($NO_2$ and $O_2$). Step 1105 is to measure $NO_2$ sensor response at frequency $f_1$. Step 1106 is to excite the $NO_2$ sensor at frequency $f_2$. Step 1107 is to measure $NO_2$ sensor response at frequency $f_2$. Response at $f_2$ contains contributions only from the interfering species $O_2$.

Step 1108 is to use $NO_2$ sensor response at frequency $f_2$ and calibration curves to calculate concentration of interfering species $O_2$. In Step 1109 concentration of 'interfering species $O_2$' may also be considered an 'output.'

Step 1110 is to use $NO_2$ sensor response at frequency $f_1$, calculated concentration of interfering species $O_2$ and calibration curves to calculate concentration of species of interest NO. Step 1111 provides output concentration of species of interest $NO_2$.

The method 1100 illustrated in FIG. 11 is a computer implemented multiple frequency method for the operation of a $NO_2$ sensor to measure a parameter of interest using calibration curves, wherein interfering parameters may be present. The method 1100 illustrated in FIG. 11 includes the step 1104 of exciting the $NO_2$ sensor at a first frequency providing a first $NO_2$ sensor response from both species of interest and interfering species ($NO_2$ and $O_2$) recorded on a computer-readable medium, the step 1106 exciting the $NO_2$ sensor at a second frequency providing a second $NO_2$ sensor response recorded on a computer-readable medium, the step 1108 using said second NO sensor response at said second frequency from both species of interest and interfering species ($NO_2$ and $O_2$) and the calibration information to produce a calculated concentration of the interfering parameters $O_2$ recorded on a computer-readable medium, and the step 1110 using said first $NO_2$ sensor response at said first frequency, said calculated concentration of the interfering parameters $O_2$, and the calibration information to measure the parameter of interest $NO_2$.

Sensing Method for Measuring NO in a Background Varying $O_2$

Figure 12:
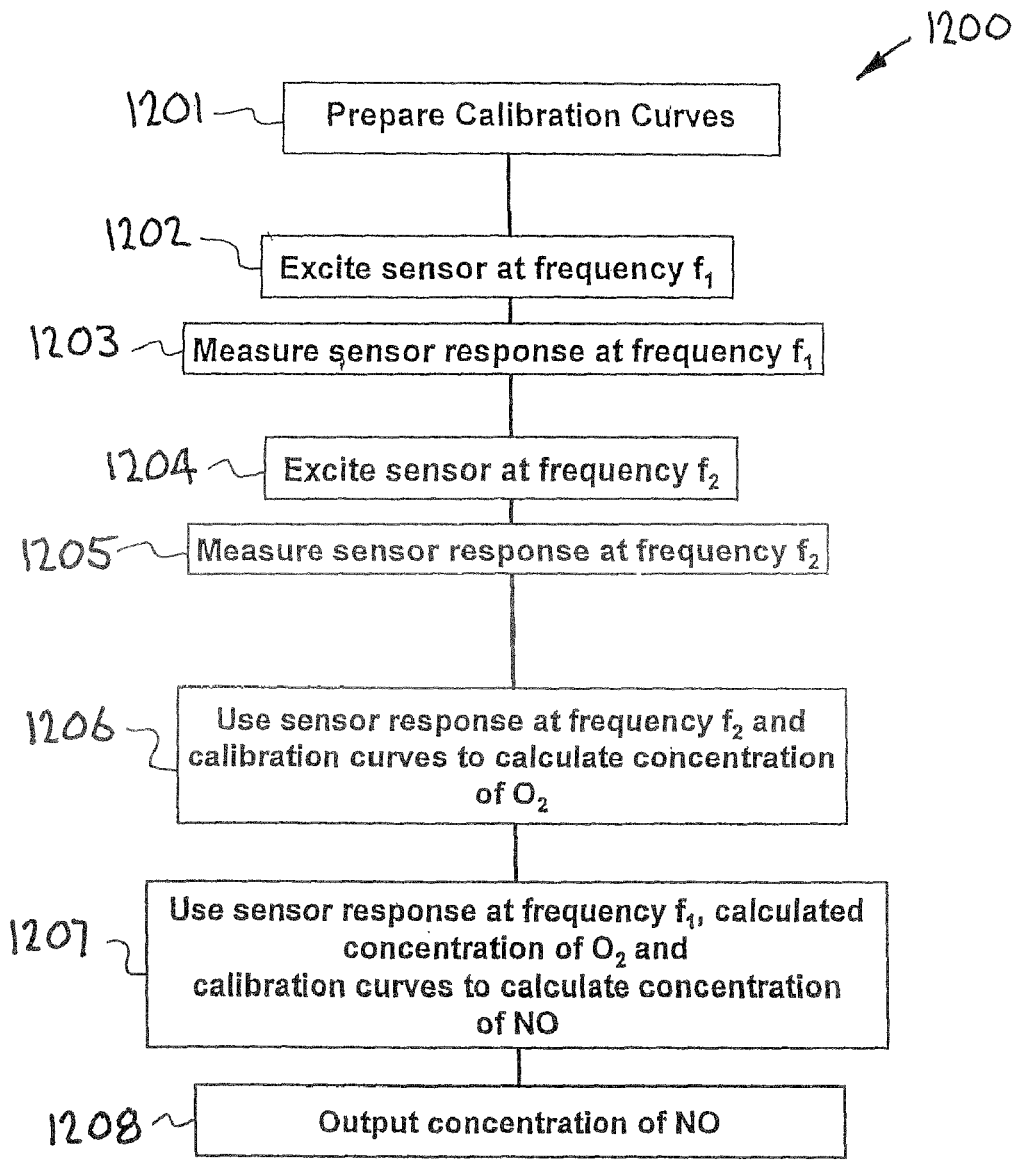
FIG. 12 illustrates a sensing method for measuring NO in a background with varying $O_2$ concentration.

Referring now to FIG. 12, an embodiment of a sensing method for measuring NO in a background with varying $O_2$ concentration is illustrated. This embodiment of the present invention is designated generally by the reference numeral 1200. The method 1200 includes the steps of exciting the sensor at a first frequency producing a first frequency sensor response, measuring the first frequency sensor response producing a first frequency sensor measurement, exciting the sensor at a second frequency producing a second frequency sensor response, measuring the second frequency sensor response producing a second frequency sensor measurement, using the second frequency sensor measurement and the calibration information to produce a calculated concentration of $O_2$ measurement, and using the first frequency sensor measurement, the calculated concentration of $O_2$ measurement, and the calibration information to measure NO.

The method 1200 is an embodiment of the multiple frequency method for the operation of a NO sensor trying to measure the concentration of NO in a background with varying $O_2$ concentration. The actual sensing element is designed so that the relative sensitivities to NO and $O_2$ are different at two different frequencies—$f_1$ and $f_2$. The method 1200 includes the following steps: Step 1201 is to generate calibration curves. Step 1201 is performed prior to NO sensor operation. Step 1202 is to excite the NO sensor at frequency $f_1$. Response at $f_1$ contains contributions from both NO and $O_2$. Step 1203 is to measure NO sensor response at frequency $f_1$. Step 1204 is to excite the NO sensor at frequency $f_2$. Step 1205 is to measure NO sensor response at frequency $f_2$. Response at $f_2$ contains contributions only from $O_2$. Step 1206 is to use NO sensor response at frequency $f_2$ and the calibration curves to calculate the concentration of interfering $O_2$. Step 1207 is to use NO sensor response at frequency $f_1$, calculated concentration of interfering $O_2$ and the calibration curves to calculate concentration of NO. Step 1208 provides output concentration of NO.

In summary, the method 1200 is sensing method to measure NO using calibration information wherein varying amount of $O_2$ may be present. The method 1200 includes the steps of exciting the sensor at a first frequency producing a first frequency sensor response that includes both NO and $O_2$, measuring the first frequency sensor response that includes both NO and $O_2$ producing a first frequency sensor measurement that includes both NO and $O_2$, exciting the sensor at a second frequency producing a second frequency sensor response that contains only $O_2$, measuring the second frequency sensor response producing a second frequency sensor measurement that contains only $O_2$, using the second frequency sensor measurement that contains only $O_2$ and the calibration information to produce a calculated concentration of $O_2$ measurement, and using the first frequency sensor measurement includes both NO and $O_2$, the calculated concentration of $O_2$ measurement, and the calibration information to measure NO.

Sensing Method for Measuring CO in a Background Varying $O_2$

Figure 13:
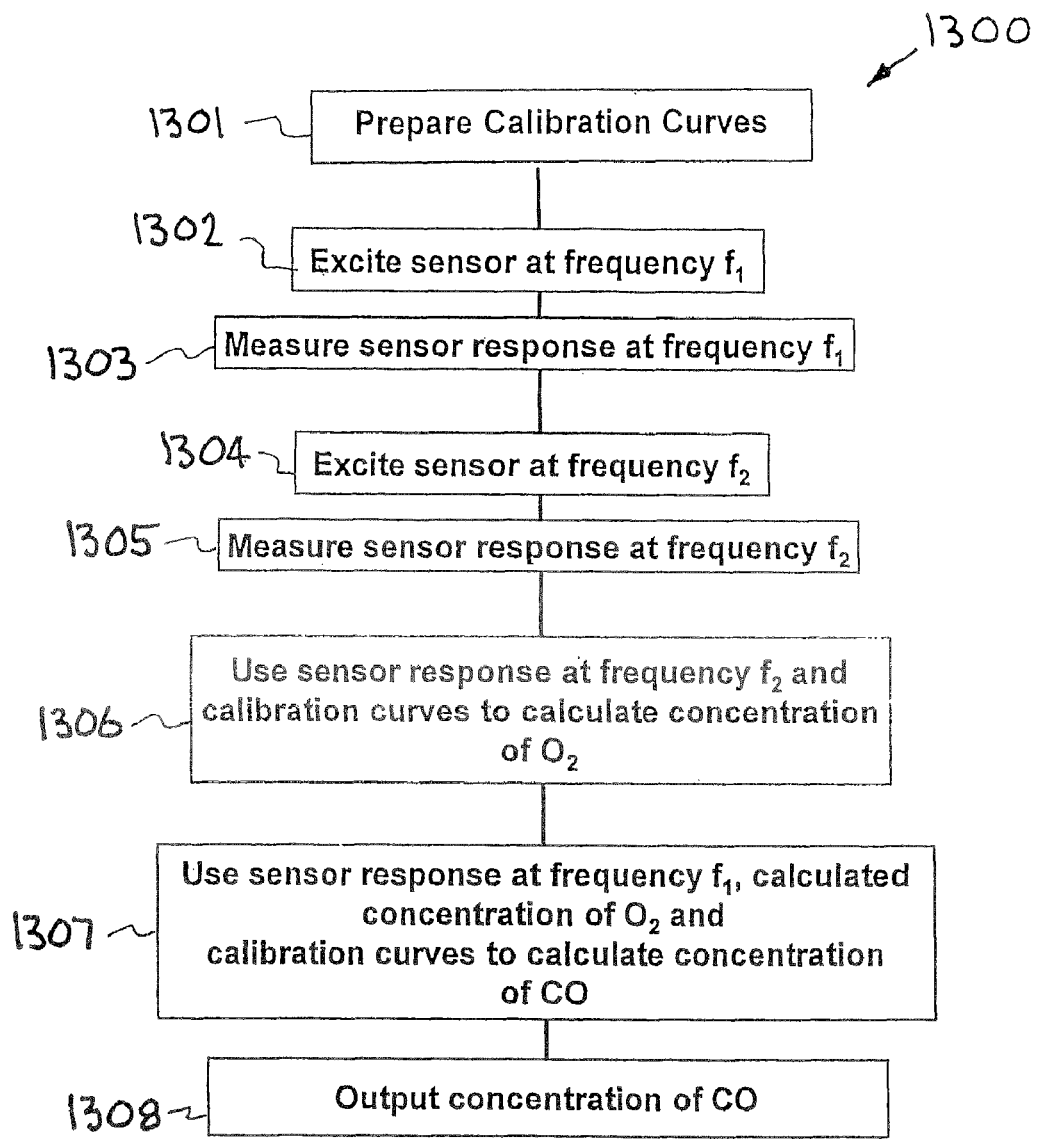
FIG. 13 illustrates a sensing method for measuring CO in a background with varying $O_2$ concentration.

Referring now to FIG. 13, an embodiment of a sensing method for measuring CO in a background with varying $O_2$ concentration is illustrated. This embodiment of the present invention is designated generally by the reference numeral 1300. The method 1300 includes the steps of exciting the sensor at a first frequency producing a first frequency sensor response, measuring the first frequency sensor response producing a first frequency sensor measurement, exciting the sensor at a second frequency producing a second frequency sensor response, measuring the second frequency sensor response producing a second frequency sensor measurement, using the second frequency sensor measurement and the calibration information to produce a calculated concentration of $O_2$ measurement, and using the first frequency sensor measurement, the calculated concentration of $O_2$ measurement, and the calibration information to measure CO.

The method 1300 is an embodiment of the multiple frequency method for the operation of a CO sensor trying to measure the concentration of CO in a background with varying $O_2$ concentration. The actual sensing element is designed so that the relative sensitivities to CO and $O_2$ are different at two different frequencies—$f_1$ and $f_2$. The method 1300 includes the following steps: Step 1301 is to generate calibration curves. Step 1301 is performed prior to CO sensor operation. Step 1302 is to excite the CO sensor at frequency $f_1$. Response at $f_1$ contains contributions from both CO and $O_2$. Step 1303 is to measure CO sensor response at frequency $f_1$. Step 1304 is to excite the CO sensor at frequency $f_2$. Step 1305 is to measure CO sensor response at frequency $f_2$. Response at $f_2$ contains contributions only from $O_2$. Step 1306 is to use CO sensor response at frequency $f_2$ and the calibration curves to calculate the concentration of interfering $O_2$. Step 1307 is to use CO sensor response at frequency $f_1$, calculated concentration of interfering $O_2$ and the calibration curves to calculate concentration of CO. Step 1308 provides output concentration of CO.

In summary, the method 1300 is a sensing method to measure CO using calibration information wherein varying amount of $O_2$ may be present. The method 1300 includes the steps of exciting the sensor at a first frequency producing a first frequency sensor response that includes both CO and $O_2$, measuring the first frequency sensor response that includes both CO and $O_2$ producing a first frequency sensor measurement that includes both CO and $O_2$, exciting the sensor at a second frequency producing a second frequency sensor response that contains only $O_2$, measuring the second frequency sensor response producing a second frequency sensor measurement that contains only $O_2$, using the second frequency sensor measurement that contains only $O_2$ and the calibration information to produce a calculated concentration of $O_2$ measurement, and using the first frequency sensor measurement includes both CO and $O_2$, the calculated concentration of $O_2$ measurement, and the calibration information to measure CO.

Sensing Method for Measuring NO in a Background of Varying Temperature

Figure 14:
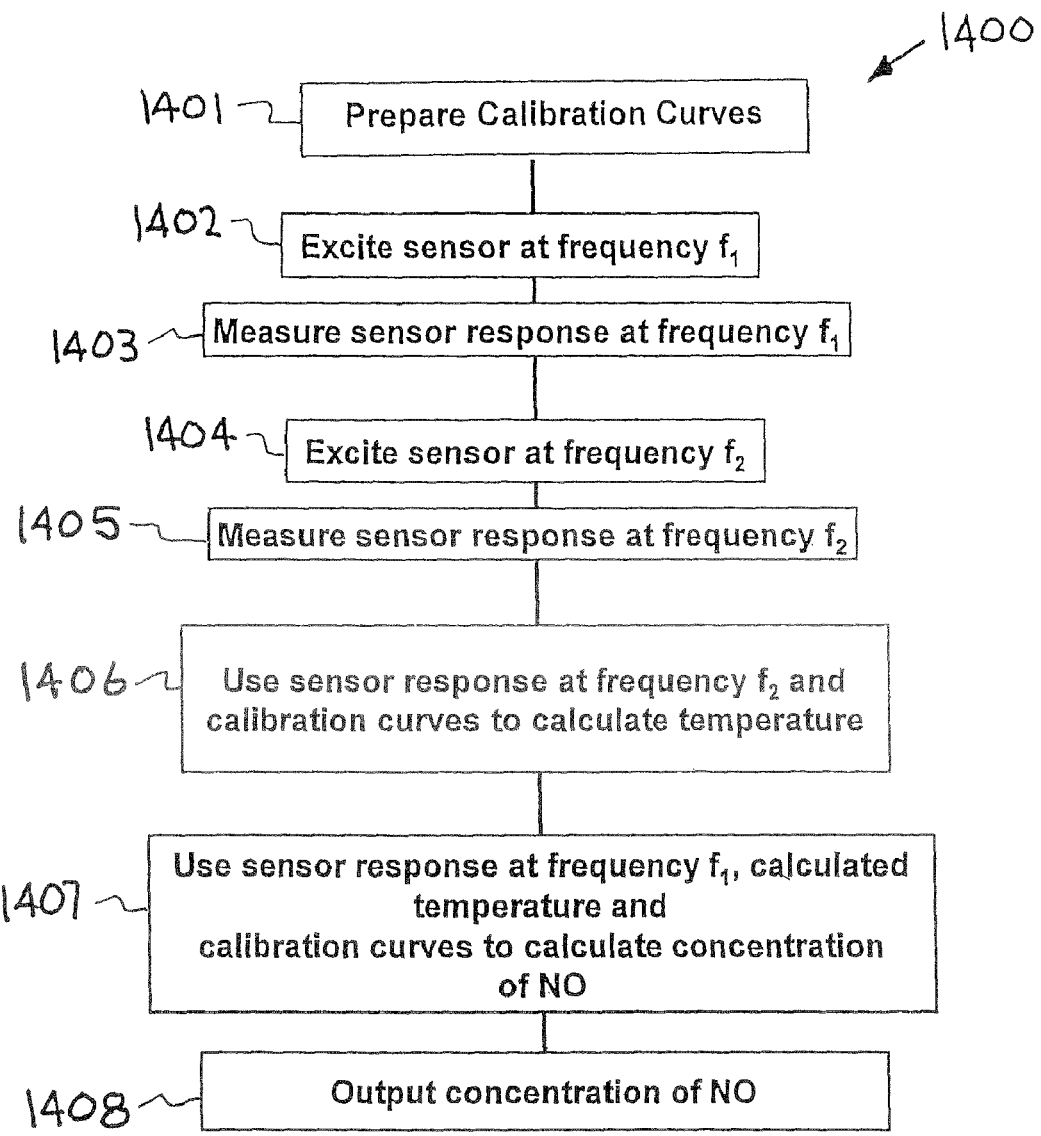
FIG. 14 illustrates a sensing method for measuring NO in a background with varying temperature.

Referring now to FIG. 14, an embodiment of a sensing method for measuring NO in a background with varying temperature is illustrated. This embodiment of the present invention is designated generally by the reference numeral 1400. The method 1400 includes the steps of exciting the sensor at a first frequency producing a first frequency sensor response, measuring the first frequency sensor response producing a first frequency sensor measurement, exciting the sensor at a second frequency producing a second frequency sensor response, measuring the second frequency sensor response producing a second frequency sensor measurement, using the second frequency sensor measurement and the calibration information to produce a calculated temperature measurement, and using the first frequency sensor measurement, the calculated temperature measurement, and the calibration information to measure NO.

The method 1400 is an embodiment of the multiple frequency method for the operation of a NO sensor trying to measure the concentration of NO in a background with varying temperature. The actual sensing element is designed so that the relative sensitivities to NO and temperature are different at two different frequencies—$f_1$ and $f_2$. The method 1400 includes the following steps: Step 1401 is to generate calibration curves. Step 1401 is performed prior to NO sensor operation. Step 1402 is to excite the NO sensor at frequency $f_1$. Response at $f_1$ contains contributions from both NO and temperature. Step 1403 is to measure NO sensor response at frequency $f_1$. Step 1404 is to excite the NO sensor at frequency $f_2$. Step 1405 is to measure NO sensor response at frequency $f_2$. Response at $f_2$ contains contributions only from temperature. Step 1406 is to use NO sensor response at frequency $f_2$ and the calibration curves to calculate temperature. Step 1407 is to use NO sensor response at frequency $f_1$, calculated temperature and the calibration curves to calculate concentration of NO. Step 1408 provides output concentration of NO.

In summary, the method 1400 is sensing method to measure NO using calibration information wherein varying temperature may be present. The method 1400 includes the steps of exciting the sensor at a first frequency producing a first frequency sensor response that includes both NO and temperature, measuring the first frequency sensor response that includes both NO and temperature producing a first frequency sensor measurement that includes both NO and temperature, exciting the sensor at a second frequency producing a second frequency sensor response that contains only temperature, measuring the second frequency sensor response producing a second frequency sensor measurement that contains only temperature, using the second frequency sensor measurement that contains only temperature and the calibration information to produce a calculated temperature measurement, and using the first frequency sensor measurement includes both NO and temperature, the calculated temperature measurement, and the calibration information to measure NO.

Sensing Method for Measuring $NO_2$ in a Background Varying $O_2$

Figure 15:
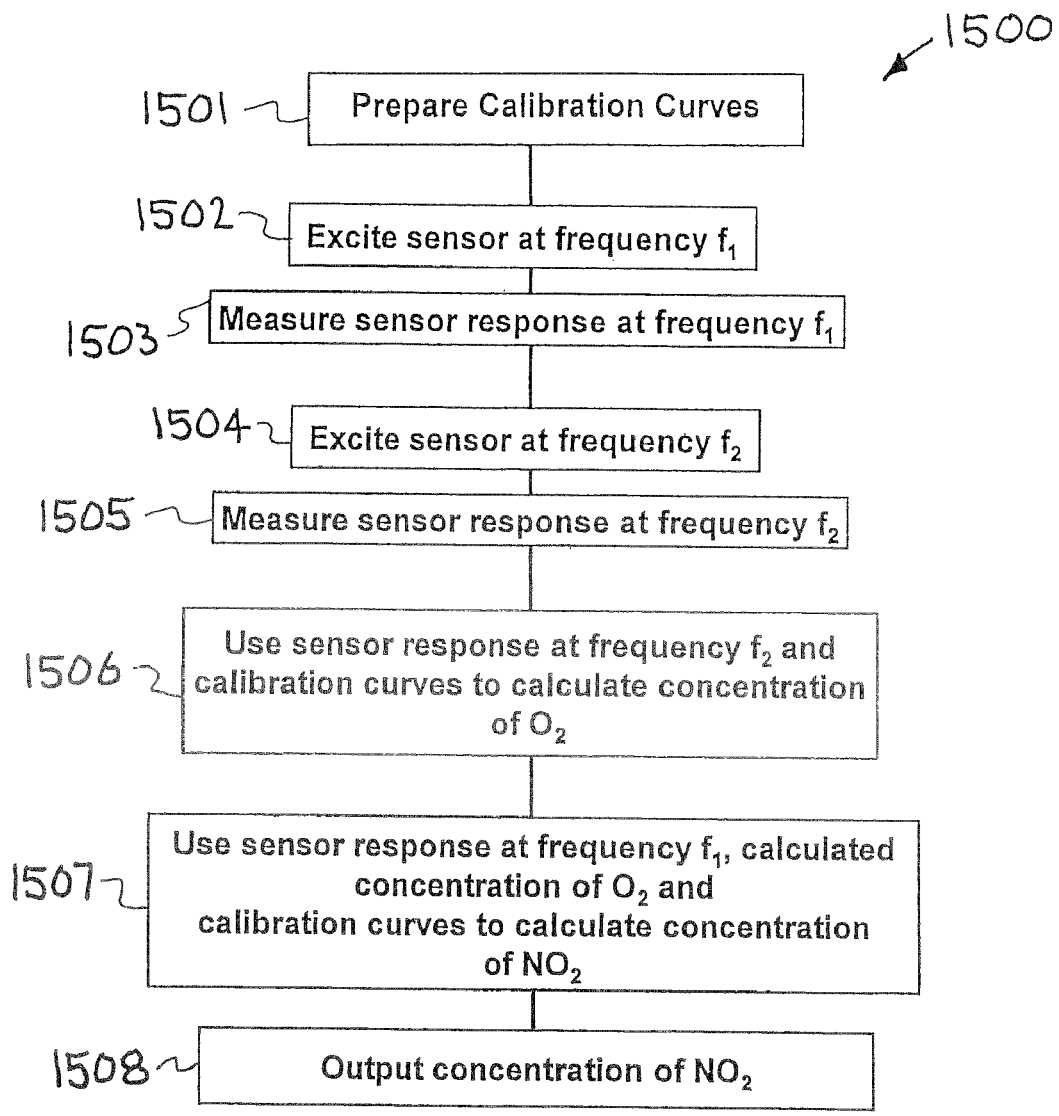
FIG. 15 illustrates a sensing method for measuring $NO_2$ in a background with varying $O_2$ concentration.

Referring now to FIG. 15, an embodiment of a sensing method for measuring $NO_2$ in a background with varying $O_2$ concentration is illustrated. This embodiment of the present invention is designated generally by the reference numeral 1500. The method 1500 includes the steps of exciting the sensor at a first frequency producing a first frequency sensor response, measuring the first frequency sensor response producing a first frequency sensor measurement, exciting the sensor at a second frequency producing a second frequency sensor response, measuring the second frequency sensor response producing a second frequency sensor measurement, using the second frequency sensor measurement and the calibration information to produce a calculated concentration of $O_2$ measurement, and using the first frequency sensor measurement, the calculated concentration of $O_2$ measurement, and the calibration information to measure $NO_2$.

The method 1500 is an embodiment of the multiple frequency method for the operation of a $NO_2$ sensor trying to measure the concentration of $NO_2$ in a background with varying $O_2$ concentration. The actual sensing element is designed so that the relative sensitivities to $NO_2$ and $O_2$ are different at two different frequencies—$f_1$ and $f_2$. The method 1500 includes the following steps: Step 1501 is to generate calibration curves Steps is performed prior to $NO_2$ sensor operation. Step 1502 is to excite the $NO_2$ sensor at frequency $f_1$. Response at $f_1$ contains contributions from both $NO_2$ and $O_2$. Step 1503 is to measure $NO_2$ sensor response at frequency $f_1$. Step 1504 is to excite the $NO_2$ sensor at frequency $f_2$. Step 1505 is to measure $NO_2$ sensor response at frequency $f_2$. Response at $f_2$ contains contributions only from $O_2$. Step

1506 is to use $NO_2$ sensor response at frequency $f_2$ and the calibration curves to calculate the concentration of interfering $O_2$. Step 1507 is to use $NO_2$ sensor response at frequency $f_1$, calculated concentration of interfering $O_2$ and the calibration curves to calculate concentration of $NO_2$. Step 1508 provides output concentration of $NO_2$.

In summary, the method 1500 is sensing method to measure $NO_2$ using calibration information wherein varying amount of $O_2$ may be present. The method 1500 includes the steps of exciting the sensor at a first frequency producing a first frequency sensor response that includes both $NO_2$ and $O_2$, measuring the first frequency sensor response that includes both $NO_2$ and $O_2$ producing a first frequency sensor measurement that includes both $NO_2$ and $O_2$, exciting the sensor at a second frequency producing a second frequency sensor response that contains only $O_2$, measuring the second frequency sensor response producing a second frequency sensor measurement that contains only $O_2$, using the second frequency sensor measurement that contains only $O_2$ and the calibration information to produce a calculated concentration of $O_2$ measurement, and using the first frequency sensor measurement includes both $NO_2$ and $O_2$, the calculated concentration of $O_2$ measurement, and the calibration information to measure $NO_2$.

Additional details of the present invention were included in United States Provisional Patent Application No. 60/839,500 filed Aug. 22, 2006 and titled "Multiple Frequency Technique for Operation of Electrochemical Sensors" and those additional details were incorporated into this application by reference. Portions of United States Provisional Patent Application No. 60/839,500 filed Aug. 22, 2006 are provided below to more fully describe the subject invention.

An important aspect of the subject invention is the issue of the frequency of operation. It has been stated that by operating at ~10 Hz provides good sensitivity to $NO_x$ gas. Actually, sensitivity is typically higher at lower frequencies, which is why the work of Miura reports, sensing at 1 Hz; due to a combination of their sensor properties, and their measurement of |Z| rather than phase, they cannot operate at a significantly higher frequency. However it is probably not practical to attempt to deploy a sensor operating on a fixed frequency below ~5 Hz. Also the frequency determines response and sampling times (with 1/frequency representing a general limitation for the sampling rate). Thus, it is desirable to operate at the highest frequency at which, sufficient sensitivity can be obtained. At much higher frequencies, however, such as 1000 Hz or more the sensor has no response to (in Applicant's case) $NO_x$ but rather responds only to changes in the $O_2$ background, temperature, and other interfering effects. This provides the third point of novelty of the proposed sensor . . . that the sensor can be simultaneously operated at two (or more) widely different frequencies to provide a compensation for these interfering effects. That is, for example, at 10 Hz the sensor senses both changes in the concentrations of NOx and $O_2$, while at 1000 Hz it senses only the changes in $O_2$. Thus, by comparing these signals the competing effects of variations of several percent in the $O_2$ background can be from the effects of ppm changes in the $NO_x$ concentration.

Sensor testing was performed in a quartz tube heated in a tube furnace to 600° C. In the test configuration, both electrodes were exposed to the gas flow, i.e. there is no external reference electrode, and the gas composition was controlled by mixing air, $N_2$, and 100 ppm NO or $NO_2$ in $N_2$, using a standard gas handling system equipped with thermal mass flow controllers. Gas flow rate was maintained at 500 ml/min for all compositions. Au foil was overlaid on top of the sensor electrodes to provide electrical coupling to the external circuit. To insure uniform and effective contact, the foil was held in place by an $Al_2O_3$ flat placed on top of the foils and spring-loaded to apply a constant pressure to the foil/electrodes.

Figure 16:
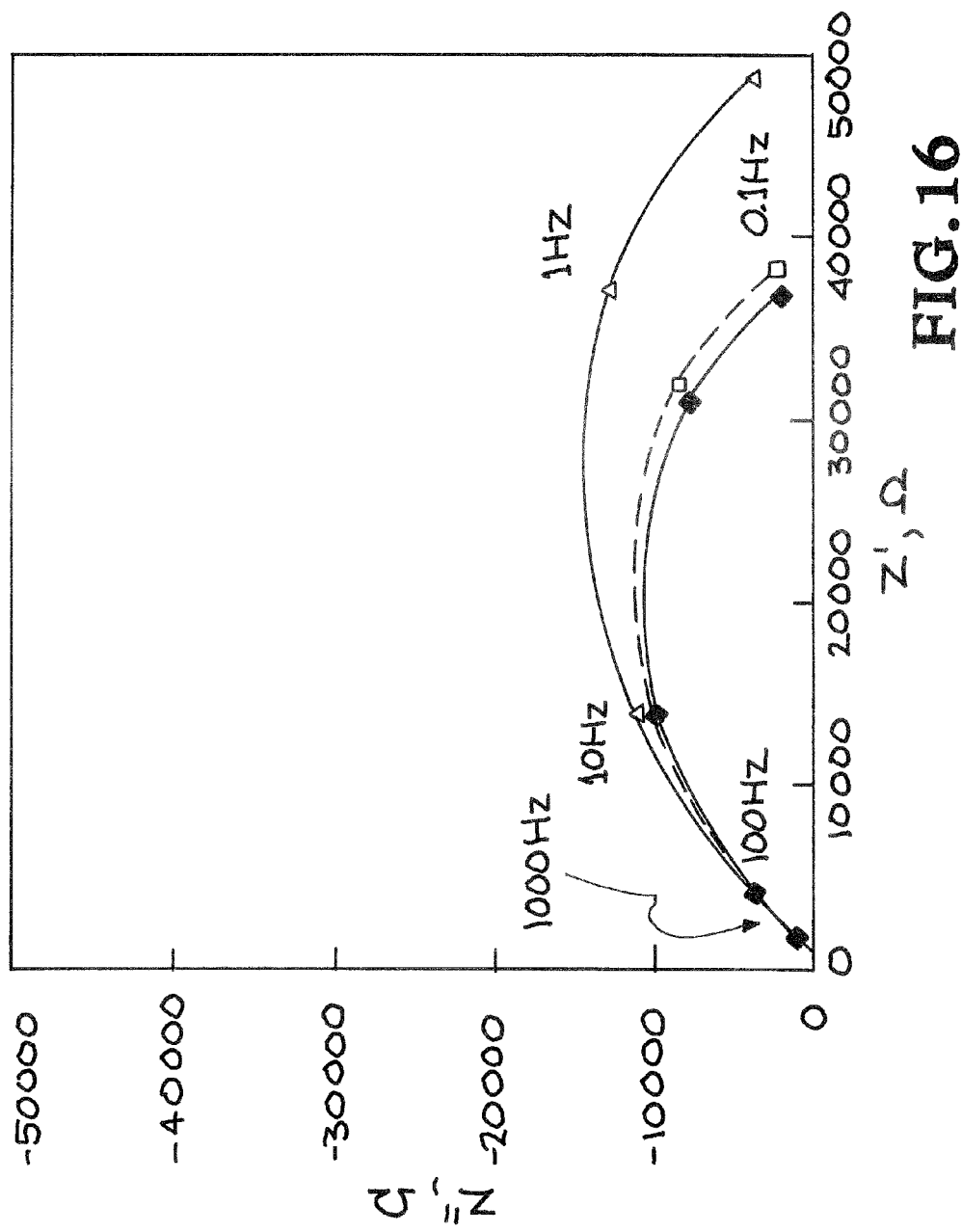
FIG. 16 is a Nyquist plot showing the impedance spectrum for the sensor at 600° C. in 10.5% $O_2$, and in 10.5% $O_2$ mixed with 100 ppm NO and 100 ppm $NO_2$. The excitation voltage is 50 m V rms.

FIG. 16 shows the impedance spectrum for the sensor at 600° C. in 10.5% $O_2$. Also shown are the spectra for 100 ppm concentrations of NO and $NO_2$ at the same $O_2$ concentration. The spectra were acquired using an excitation voltage of 50 mV rms by stepping the frequency from 100 kHz to 0.1 Hz, with a frequency resolution of 20 steps/decade. Points corresponding to 0.1, 1.0, 10, 100, and 1000 Hz are marked on each spectrum. The data indicate that the cell has a high dc impedance of approximately 50 kΩ, and that the dc impedance decreases markedly with the introduction of $NO_x$ to the gas stream. Two arcs are observed within the frequency range; a small arc at high frequencies above ~100 kHz (too small to be visible in FIG. 16), and the large arc visible in FIG. 16 below 1 kHz. The small, high frequency arc is insensitive to the presence of $NO_x$, however the large, low frequency arc is significantly altered in the presence of $NO_x$. Others have seen qualitatively similar impedance behavior using $ZnCr_2O_4$ sensing electrodes to detect $NO_x$, and Au-$Ga_2O_3$ sensing electrodes to detect CO, respectively. The response of the $ZnCr_2O_4$ was attributed to possible changes in the electrode-interface resistance due to interactions such as adsorption and reactions occurring at the interface. It should be noted that for the $ZnCr_2O_4$ sensing electrodes, the counter electrode was a Pt reference electrode exposed to atmospheric air, while only the sensing electrode was exposed to the test atmosphere with different concentrations of $NO_x$. For the CO sensor, the Au—$Ga_2O_3$ sensing electrode and Pt reference electrode were both exposed to the same testing atmosphere and changes in charge transfer kinetics at the electrolyte/electrode interface were proposed to explain the impedance behavior.

All three spectra in FIG. 16 demonstrate similar high-frequency behavior (100 Hz), which is dominated by the properties of the bulk YSZ electrolyte/substrate (i.e., conductivity and dielectric constant). The response to NOx manifests at frequencies <100 Hz by a decrease in the diameter of the large, lower-frequency arc. The non-ideal shape (i.e., deviation from semicircular arcs) of the Nyquist plots are likely due to a convolution of various processes which could include diffusion, charge transfer, and adsorption/desorption, in addition to heterogeneities in bulk and interfacial properties. A detailed study of the possible mechanisms involved is beyond the scope of the subject application and is the focus of a separate study currently in progress. However, a preliminary equivalent-circuit analysis of the Nyquist data was performed in order to provide insight into the operation of the sensor in an impedancemetric mode.

Figure 17:
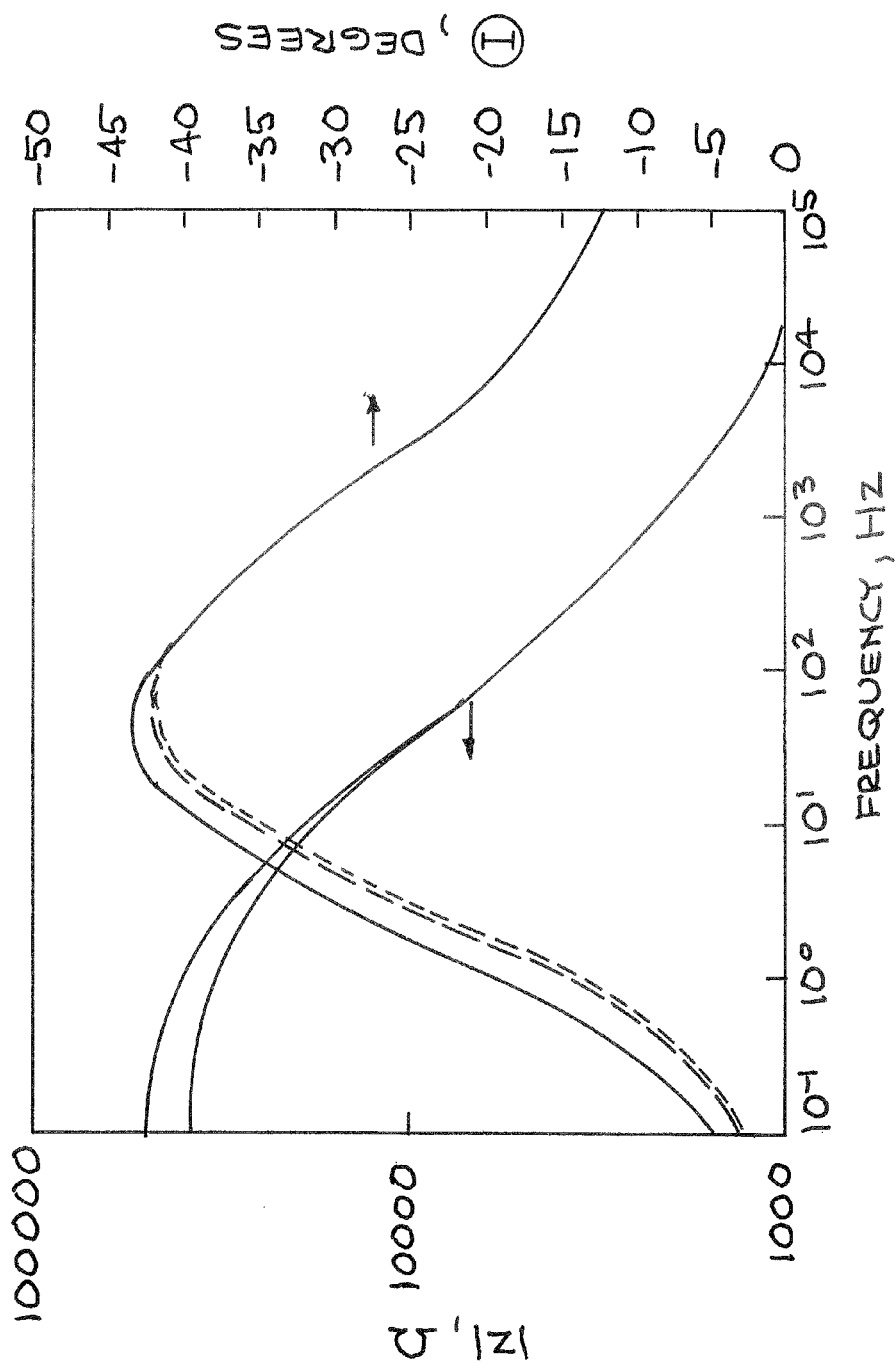
FIG. 17 is a Bode plot of the impedance spectrum for the sensor at 600° C. in 10.5% $O_2$ (solid lines), and in 10.5% $O_2$ mixed with 100 ppm NO (dotted lines) and 100 ppm $NO_2$ (dashed lines).
Figure 18:
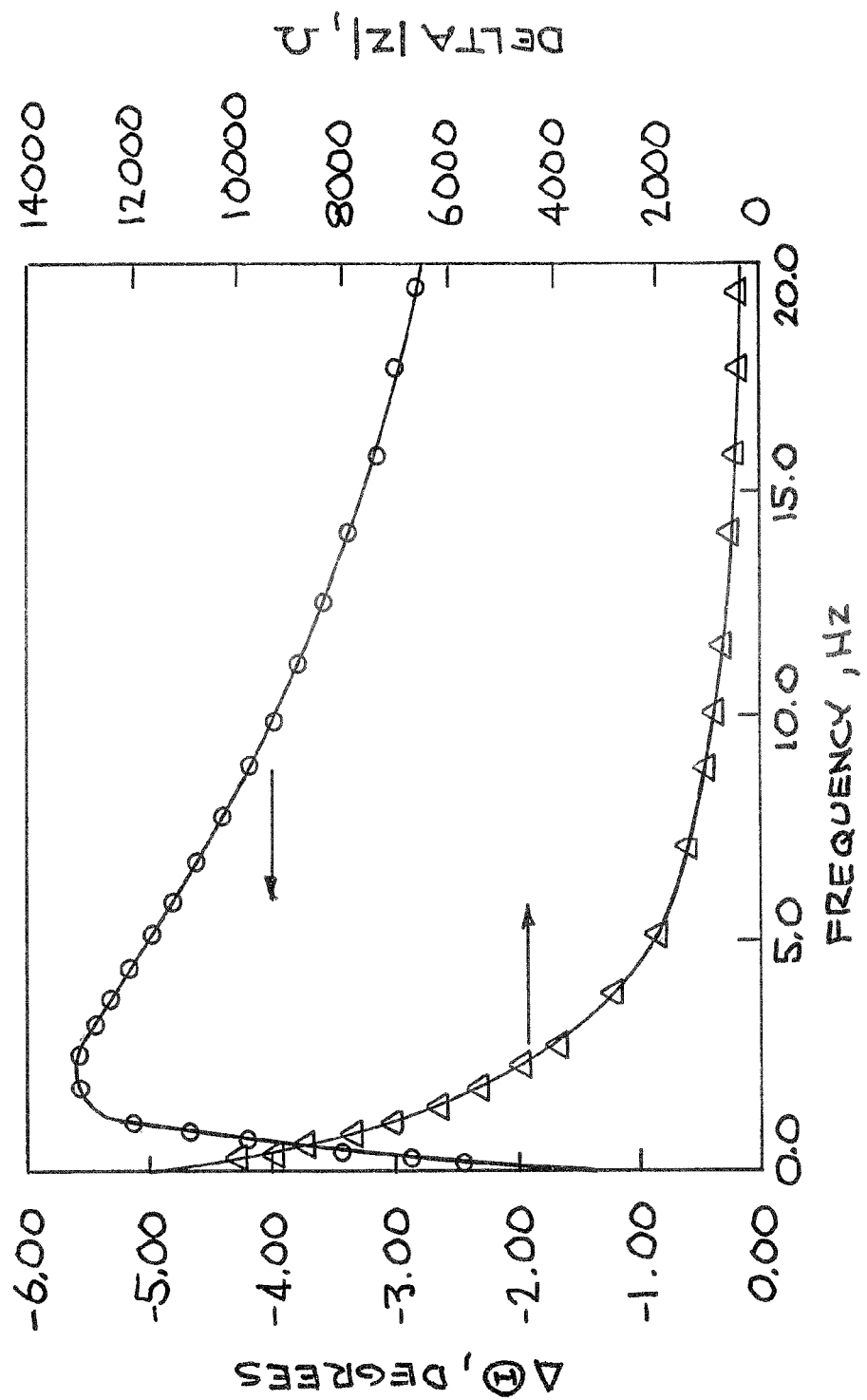
FIG. 18 illustrates the difference between the Θ measured in 10.5% $O_2$, and in 10.5% $O_2$ mixed with 100 ppm NO, from FIG. 17 Page 35 on the PRO. App.))and the difference between the |Z| measured in 10.5% $O_2$, and in 10.5% $O_2$ mixed with 100 ppm NO.

FIG. 17 shows the Bode plots of |Z| and Θ for the same impedance spectra shown in FIG. 16. It is interesting to note that the difference in the Θ associated with the presence of $NO_x$ persists to significantly higher frequency than does the change in |Z|. Of course, the shift in Θ also decays to zero as the frequency approaches dc. The net result is that the effect of $NO_x$ on the Θ reaches a maximum at approximately 2 Hz before decaying slowly with increasing frequency. In contrast, the shift in |Z| decreases rapidly with increasing frequency. This behavior is illustrated, more clearly in FIG. 18 where the Θ and |Z| data are plotted to show effect of 100 ppm NO, relative to the 10.5% $O_2$ baseline, versus frequency. FIG. 18 shows that the phase shift due to the NO addition (to the 10.5% $O_2$ background) reaches a maximum at 2 Hz, and decays with increasing frequency to reach 90 and 71% of the maximum value at 5 and 10 Hz, respectively. In contrast, the maximum measured shift in |Z| is at the lowest frequency sampled (0.1 Hz). It is expected that |Z| will continue to increase as the frequency approaches zero, at which point it will reach the dc resistance. |Z| decays with increasing frequency at all frequencies above zero, and this decay can be seen to be notably faster than for the Θ response. For example, at 5 and 10 Hz the shift in |Z| has decayed to 43 and 21%, respectively, of the value at 2 Hz (these values are given for comparison with the Θ data), and to 17 and 7.5%, respectively, of the maximum measured shift at 0.1 Hz.

The capability to monitor the NOx response, via the Θ, of this electrochemical cell at frequencies significantly higher than 1 Hz has significant implications for 'real-world' sensor applications. Increased operating frequency typically presents the opportunity for improved signal processing (i.e., noise correction), faster sensor response, and reduced sampling time (time between measurements). Also, as can be seen from FIGS. 16 and 17, at frequencies above ~100 Hz the $NO_x$ response is negligible. This presents an additional opportunity to implement a multiple-frequency mode of operation to allow for compensation from interfering effects such as fluctuating $O_2$ concentration and variations in temperature. The data presented in the next section will demonstrate how sensor operation at two distinct frequencies can be utilized to correct for wide variations in the $O_2$ concentration while maintaining high sensitivity to $NO_x$. A sensing frequency of 10 Hz was selected as a compromise between increased sensitivity (lower frequency) and reduced sampling time/improved signal-to-noise (higher frequency). This represents potentially an order of magnitude faster sampling rate than previous reports, while maintaining the capability to resolve sub-10 ppm levels of $NO_x$.

Figure 19:
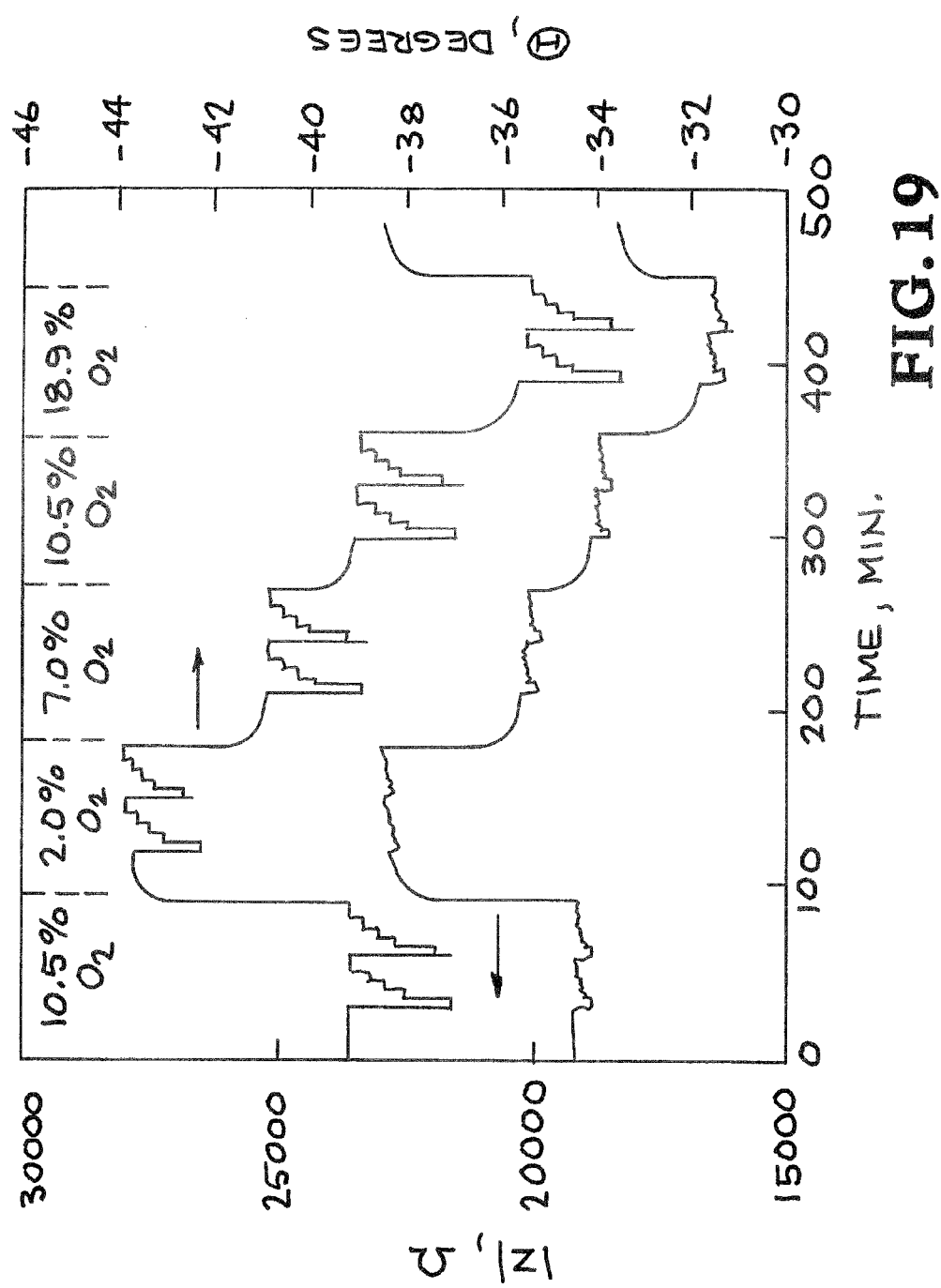
FIG. 19 shows |Z| and Θ measured at 10 Hz and 600° C. with an excitation voltage of 50 mV rms wherein the $O_2$ concentration varies from 2 (%)–18.9%, and NOx, exposures of 50, 25, 15, and 8 ppm of NO ($1^{st}$) and $NO_2$ ($2^{nd}$) are performed at each concentration.
Figure 20:
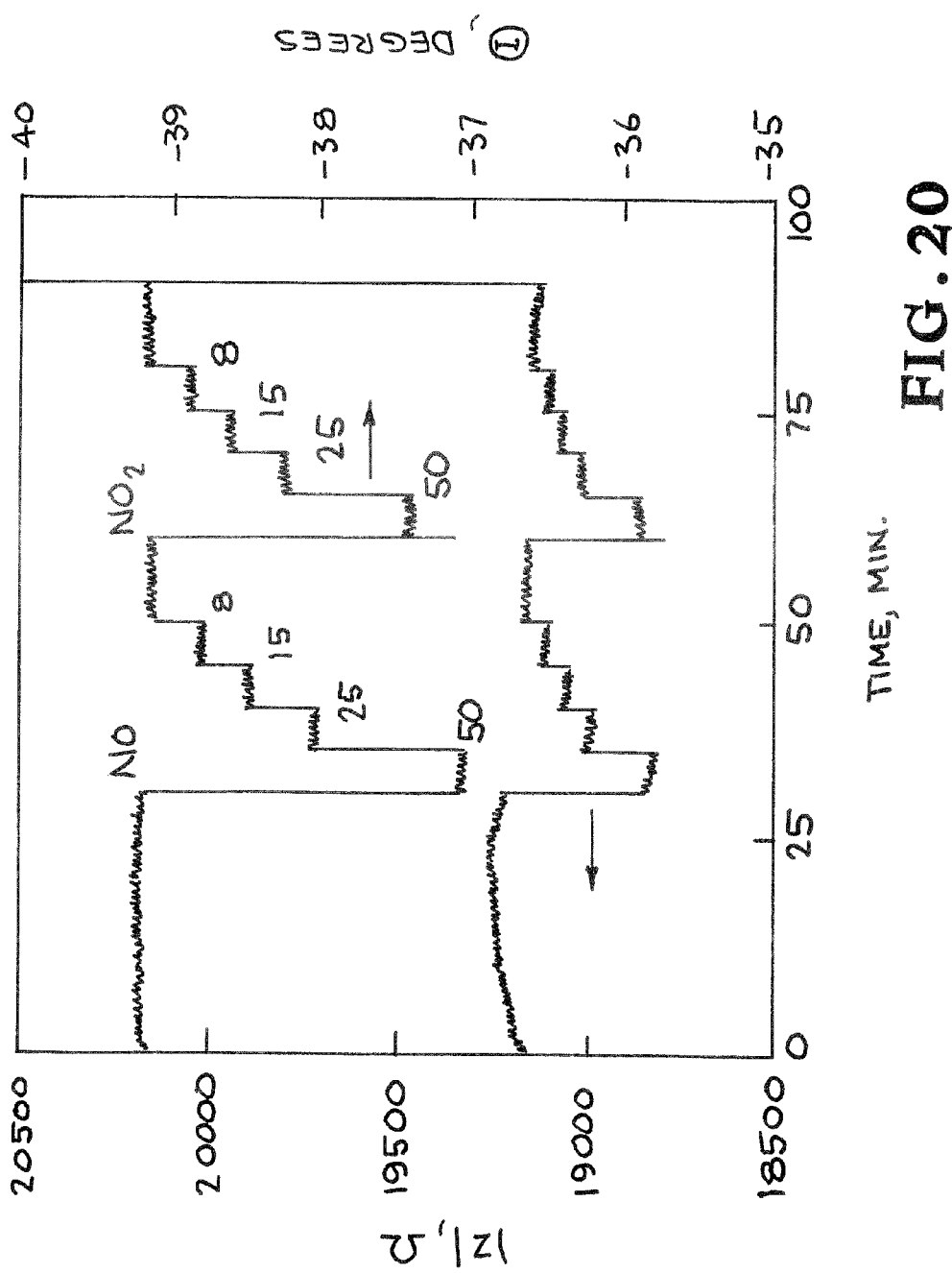
FIG. 20 is an expanded view of the $1^{st}$ 100 minutes from FIG. 17 that shows |Z| (or and Θ measured at 10 Hz in 10.5% $O_2$. $NO_1$ ($1^{st}$) and $NO_2$ ($2^{nd}$) concentrations are indicated in the FIG. (50, 25, 15, and 8 ppm).

FIG. 19 shows Θ and |Z| measured during continuous operation at 10 Hz using a 50 mV excitation voltage. The data shw the sensor response as the $O_2$ concentration is cycled through the sequence 10.5, 2.0, 7.0, 10.5 and 18.9%. At each concentration, $NO_x$ exposures are performed by introducing 50, 25, 15, and 8 ppm NO followed by the same levels of $NO_2$. The responses to these $NO_x$ additions are the stair-step signals at each $O_2$ concentration. Several aspects of these data are immediately apparent. The response to NO and $NO_2$ are comparable in magnitude, with the NO response being slightly larger. This is consistent with the impedance spectra shown in FIGS. 16 and 17. The Θ response to the $NO_x$ exposures is particularly apparent and is significantly more pronounced, relative to the changing $O_2$ signal, than the |Z| response. Also, for the Θ response, the lowest $NO_x$ levels, 8 ppm, are easily resolved at all $O_2$ concentrations. This is illustrated more clearly in FIG. 20, which shows an expanded view of the first $NO_x$ exposures at 10.5% $O_2$ in FIG.19. The Θ response in FIG. 20 can be seen to be sharp and fast, $t_{90}$~4s, with a baseline which is stable over the course of the measurements. The sharp transient at the beginning of the $NO_2$ exposure is an experimental artifact related to residual NO in the shared gas line.

In contrast to the Θ measurements, the |Z| response is somewhat less pronounced, and the signal shows a tendency to drift as a function of time indicating somewhat poorer stability than for the Θ measurement. It is not immediately clear why |Z| exhibits this reduced stability, however the comparatively smaller response (relative to the Θ) at this frequency is completely consistent with the impedance spectra shown in FIG. 16.

Figure 21:
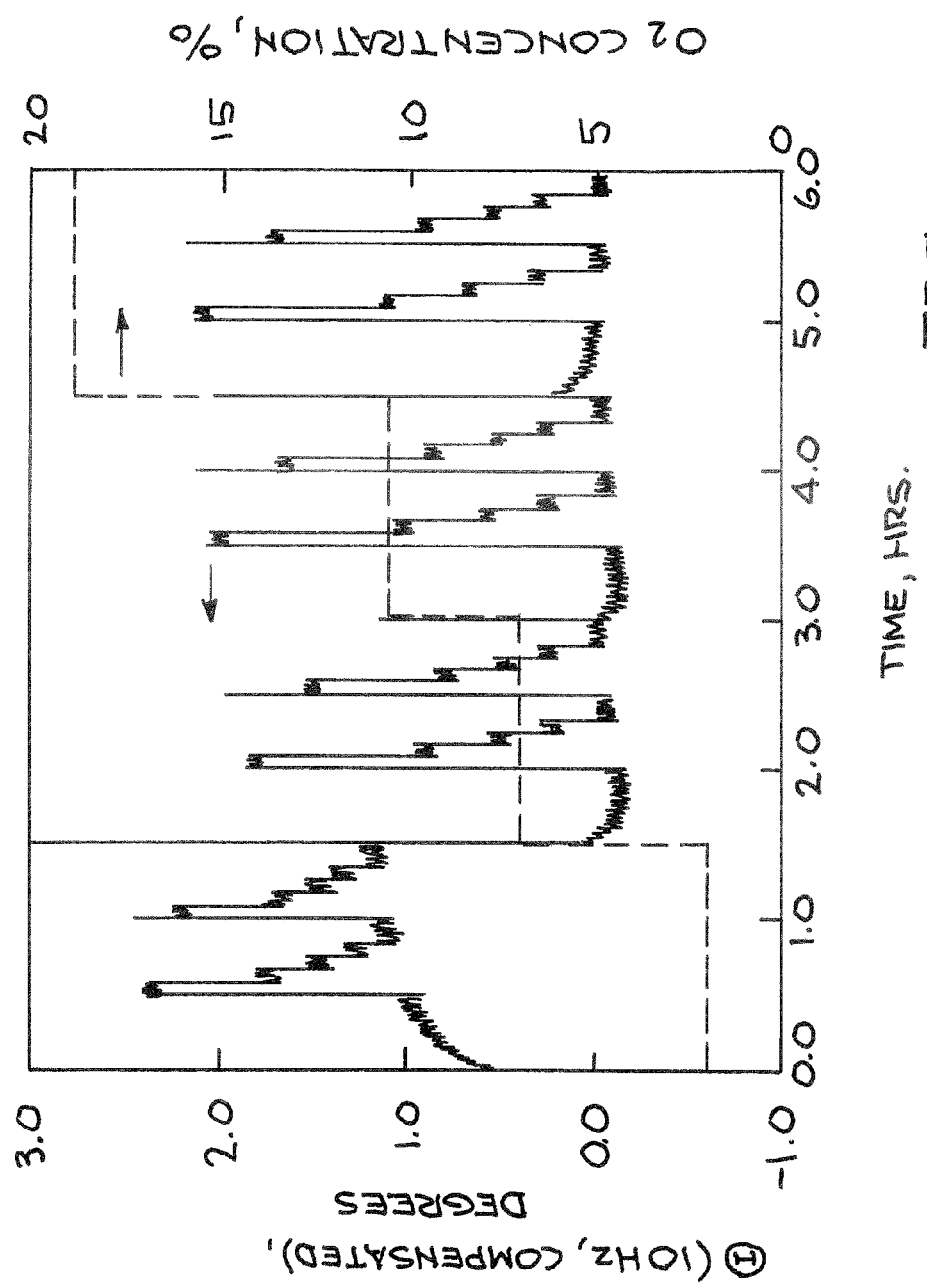
FIG. 21 shows sensor response data (10 Hz) shown in FIG. 19 compensated for the $O_2$ response.

Since the measured Θ (10 Hz) is sensitive to both $NO_x$ and $O_2$, the difference between the measured Θ and the baseline yields the $NO_x$ response. The result of this analysis is shown in FIG. 21, where the data from FIG. 19 have been numerically (point by point) corrected for the $O_2$ response. The analysis yields excellent compensation for the $O_2$ concentration at 7.0, 10.5, and 18.9% $O_2$, with clear resolution of 8 ppm levels of both NO and $NO_2$ at all three $O_2$ concentrations. At the lowest $O_2$ concentration, 2.0%, the results are not as good, however this is attributed to the slow $O_2$ response for this sensor, as previously discussed, and should be resolved by modifying the materials or structure to facilitate a faster response. It should be noted that the measurements at the two frequencies were not made simultaneously, but rather concurrently. As a result, some interpolation and time shifting had to be performed in order to align the data temporally for the analysis. This leads to transient effects were the signal changes rapidly, for example where the $O_2$ concentration is stepped. In a real application, it is envisioned that sensor operation would be accomplished instead by simultaneous excitation of the sensor using a mixed signal containing components at both frequencies (10 and 1000 Hz), thus allowing real-time correction and reducing transient artifacts associated with the data manipulation.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A multiple frequency method for the operation of an electrochemical gas sensor to measure NO using calibration information, wherein interfering parameters of $O_2$ may be present, comprising the steps of:
    providing a NO sensor,
    exciting said NO sensor at a first frequency providing a first sensor response, wherein said first frequency is non-zero,
    providing a $O_2$ sensor,
    exciting said $O_2$ sensor at a second frequency providing a second sensor response, wherein said second frequency is non-zero,
    using said second sensor response at said second frequency and the calibration information to produce a calculated concentration of the interfering parameters of $O_2$, and
    using said first sensor response at said first frequency, said calculated concentration of the interfering parameters of $O_2$, and the calibration information to measure the NO.

2. The multiple frequency method for the operation of an electrochemical gas sensor of claim 1,
    wherein said step of exciting said NO sensor at a first frequency providing a first sensor response comprises exciting said NO sensor at a first frequency providing a first sensor response recorded on a computer-readable medium,
    wherein said step of exciting said $O_2$ sensor at a second frequency providing a second sensor response comprises exciting said $O_2$ sensor at a second frequency providing a second sensor response recorded on a computer-readable medium, and
    wherein said step of using said second sensor response at said second frequency and the calibration information to produce a calculated concentration of the interfering parameters of $O_2$ comprises using said second sensor response at said second frequency and the calibration information to produce a calculated concentration of the interfering parameters of $O_2$ recorded on a computer-readable medium.

3. The multiple frequency method for the operation of an electrochemical gas sensor of claim 1,
wherein the interfering parameters of $O_2$, are varying $O_2$ concentration.

4. A multiple frequency method for the operation of an electrochemical gas sensor, to measure is $NO_2$ using calibration information, wherein interfering parameters of $O_2$ may be present, comprising the steps of:
providing a $NO_2$ sensor,
exciting said $NO_2$ sensor at a first frequency providing a first sensor response, wherein said first frequency is non-zero,
providing a $O_2$ sensor,
exciting said $O_2$ sensor at a second frequency providing a second sensor response, wherein said second frequency is non-zero,
using said $O_2$ sensor response at a second frequency and the calibration information to produce a calculated concentration of the interfering parameters of $O_2$ to produce a calculated concentration of the interfering parameters of $O_2$, and
using said first sensor response at said first frequency, said calculated concentration of the interfering parameters, and the calibration information to measure the $NO_2$.

5. A method of sensing to measure NO using calibration information wherein interfering parameters of $O_2$ may be present, comprising the steps of:
providing a NO sensor,
exciting said NO sensor at a first frequency, wherein said first frequency is non-zero,
using said NO sensor excited at a first frequency to provide a first sensor response,
providing a $O_2$ sensor,
exciting said $O_2$ sensor at a second frequency providing a second sensor response, wherein said second frequency is non-zero,
using said $O_2$ sensor excited at a second frequency to provide a second sensor response,
using said second $O_2$ sensor response at said second frequency and the calibration information to produce a calculated concentration of the interfering parameters of $O_2$, and
using said NO sensor response at said first frequency, said calculated concentration of the interfering parameters, and the calibration information to measure the NO.

6. A sensing method for measuring NO using calibration information, wherein varying amount of $O_2$ may be present, comprising the steps of:
providing a NO sensor,
exciting said NO sensor at a first frequency producing a first frequency sensor response that includes both NO and $O_2$, wherein said first frequency is non-zero,
measuring said first frequency sensor response that includes both NO and $O_2$ producing a first frequency sensor measurement that includes both NO and $O_2$,
providing a $O_2$ sensor,
exciting said $O_2$ sensor at a second frequency producing a second frequency sensor response that contains only $O_2$, wherein said second frequency is non-zero,
measuring said second frequency sensor response producing a second frequency sensor measurement that contains only $O_2$,
using said second frequency sensor measurement that contains only $O_2$ and the calibration information to produce a calculated concentration of $O_2$ measurement, and
using said first frequency sensor measurement includes both NO and $O_2$, said calculated concentration of $O_2$ measurement, and the calibration information for measuring NO.

* * * * *